United States Patent
McFadden et al.

(10) Patent No.: US 12,208,167 B1
(45) Date of Patent: Jan. 28, 2025

(54) COATED TABLETS FOR PH-DEPENDENT RELEASE OF BENZGALANTAMINE

(71) Applicant: ALPHA COGNITION INC., Vancouver (CA)

(72) Inventors: Michael McFadden, Frisco, TX (US); Denis G. Kay, Stanhope (CA); Haranath Kumar Vaddi, Weston, FL (US)

(73) Assignee: ALPHA COGNITION INC., Vancouver (CA)

( * ) Notice: Subject to any disclaimer, the term of this patent is extended or adjusted under 35 U.S.C. 154(b) by 0 days.

(21) Appl. No.: 18/434,155

(22) Filed: Feb. 6, 2024

(51) Int. Cl.
*A61K 9/28* (2006.01)
*A61K 31/55* (2006.01)

(52) U.S. Cl.
CPC .......... *A61K 9/2846* (2013.01); *A61K 9/2866* (2013.01); *A61K 9/2886* (2013.01); *A61K 31/55* (2013.01)

(58) Field of Classification Search
None
See application file for complete search history.

(56) References Cited

U.S. PATENT DOCUMENTS

| | | |
|---|---|---|
| 9,763,953 B2 | 9/2017 | Maelicke |
| 10,265,325 B2 | 4/2019 | Maelicke |
| 11,077,119 B2 | 8/2021 | Maelicke |
| 11,795,176 B2 | 10/2023 | Sancilio |
| 2003/0060423 A1 * | 3/2003 | Plata-Salaman ....... A61K 31/70 514/23 |
| 2006/0034937 A1 | 2/2006 | Patel |
| 2021/0322437 A1 | 10/2021 | Maelicke |
| 2023/0416267 A1 | 12/2023 | Sancilio |

FOREIGN PATENT DOCUMENTS

| | | | |
|---|---|---|---|
| CA | 2781826 A1 * | 6/2011 | ............. A61K 31/55 |
| WO | WO 2007/039138 A1 | 4/2007 | |
| WO | WO 2009/127218 A1 | 10/2009 | |
| WO | WO 2014/016430 A1 | 1/2014 | |
| WO | WO-2022025785 A1 * | 2/2022 | ............. A61K 31/13 |
| WO | WO-2022150917 A1 * | 7/2022 | ............. A61J 1/035 |
| WO | WO 2022/236396 A1 | 11/2022 | |
| WO | WO 2023/092231 A1 | 6/2023 | |

OTHER PUBLICATIONS

Maelicke et al., "Memogain is a Galantamine Pro-drug having Dramatically Reduced Adverse Effects and Enhanced Efficacy". Journal of Molecular Neuroscience, vol. 40, No. 1-2, Jan. 1, 2010, 135-137.
Battacharya et al., "Nasal Application of the Galantamine Pro-drug Memogain Slows Down Plaque Deposition and Ameliorates Behavior in 5X Familial Alzheimer's Disease Mice", Journal of Alzheimer's disease, 2015, 46: 123-136.
Bakker et al., "Safety, pharmacokinetics, and pharmacodynamics of Gln-1062, a prodrug of galantamine", Alzheimer's Dementia, 2020, 6(1): e12093, (in 10 pages).
Bakkman et al., "First in human study with a prodrug of galatamine: Improved benefit-risk ratio?", Alzheimer's & Dementia, Jan. 20, 2016; 2(1):13-22.

* cited by examiner

*Primary Examiner* — Susan T Tran
(74) *Attorney, Agent, or Firm* — Knobbe, Martens, Olson & Bear, LLP

(57) ABSTRACT

The invention relates to a pharmaceutical composition in the form of a tablet, said tablet comprising a tablet core, wherein said core comprises benzgalantamine (ALPHA-1062) or salt thereof, and an enteric coating, wherein said enteric coating is configured for dissolution at pH 5.5 and above. Further the invention relates to the pharmaceutical composition for use in the treatment of a brain disease associated with cognitive impairment and/or with a cholinergic deficit. The invention further relates to a method for preparing the pharmaceutical composition.

25 Claims, 3 Drawing Sheets

COATED TABLETS FOR PH-DEPENDENT RELEASE OF BENZGALANTAMINE

The invention is in the field of pharmaceutical compositions comprising the active pharmaceutical ingredient benzgalantamine (also known as galantamine benzoate, GLN-1062, Memogain, ALPHA-1062).

The invention relates to a pharmaceutical composition in the form of a tablet, said tablet comprising a. a tablet core, wherein said core comprises benzgalantamine or salt thereof, and b. an enteric coating, wherein said enteric coating is configured for dissolution at pH 5.5 and above. The invention further relates to the composition being configured to release benzgalantamine after administration to a subject in the small intestine of said subject at pH 5.5 and above.

Further the invention relates to the pharmaceutical composition for use in the treatment of a brain disease associated with cognitive impairment and/or with a cholinergic deficit. The invention further relates to a method for the treatment of a brain disease associated with cognitive impairment and/or with a cholinergic deficit, comprising administering the pharmaceutical composition as described herein to a subject in need thereof.

The invention further relates to a method for preparing the pharmaceutical composition in the form of a tablet, wherein said composition is prepared by blending components of the tablet core to form a blend, compressing said blend to form a tablet core, coating said tablet core with a film coating and coating said film coating with an enteric coating.

BACKGROUND OF THE INVENTION

Galantamine, chemically known as (4aS,6R,8aS)-3-Methoxy-11-methyl-4a,5,9,10,11,12-hexahydro-6H-benzo-furo[3a,3,2-ef][2]benzazepin-6-ol (CAS 357-70-0), is a tertiary amide, belonging to the phenanthrene chemical class, which occurs naturally in bulb plants and can also be produced synthetically. Galantamine is an inhibitor of the acetylcholinesterase (AChE) and further enhances cholinergic activity by non-competitive, allosteric modulation of the nicotinic acetylcholine receptors (nAChR), in particular the α7 subtype of nAChR. This slows the degradation of acetylcholine (Ach) and increases the affinity of existing Ach for the receptor. This mechanism of action results in an improvement of the cholinergic transmission which is, e.g., impaired in Alzheimer's disease.

Galantamine was introduced as a drug for Alzheimer's disease in 2000 and now is approved in several countries worldwide. The approved indication is generally mild to moderate dementia of Alzheimer's type. It is currently available as an immediate release tablet, oral solution and extended-release capsule and tablet. It is marketed as RAZADYNE® ER in the U.S., and as REMINYL® elsewhere. Several generic equivalents have been approved by the Food and Drug Administration (FDA) and in several European countries by the European Medicines Agency (EMA). REMINYL® and RAZADYNE® ER extended-release capsules and tablets were developed to reduce the dosage regime to one capsule daily, while bioequivalence to twice-daily immediate-release tablets is maintained.

Through their primary action, cholinomimetics, such as galantamine, increase gastric acid secretion due to increased cholinergic activity. Like other cholinesterase inhibitors, the most common adverse effects of galantamine (≥5% of adverse effects), in particular when applied orally, occur within the gastrointestinal tract (GIT), including nausea, vomiting, diarrhea, dizziness, headache, and decreased appetite. The most common adverse reactions associated with discontinuation of therapy (≥1%) in galantamine-treated patients from double-blind clinical trials were nausea (6.2%), vomiting (3.3%), decreased appetite (1.5%), and dizziness (1.3%).

During oral therapy with galantamine, the initial dose administered is therefore low and then subsequently increased over a period of months, adjusted according to the level of side effects perceived as acceptable by the patient. As a consequence of the side effects, many patients thus never reach the therapeutically most effective dose or discontinue therapy altogether. The majority of adverse reactions related to the gastrointestinal tract occurred during the dose-escalation period. In those patients who experienced the most frequent adverse reaction, nausea, the median duration of the nausea was 5-7 days.

Galantamine has been chemically modified to improve its lipophilicity and thus its passage through the blood-to-brain barrier (BBB) and mucosal tissue. Galantamine derivatives and pro-drugs are described in EP 1940817 B1, WO 2009/127218 A1 and US 2009/0253654 A1.

The galantamine prodrug benzgalantamine, also termed galantamine benzoate or ALPHA-1062, chemically known as ((4aS,6R,8aS)-4a,5,9,10,11,12-hexahydro-3-methoxy-11-methyl-6H-benzofuro[3a,3,2-ef][2]benzazepin-6-benzoate gluconate), is a benzoic ester of galantamine that exhibits limited or no pharmacological activity at therapeutic doses, until it is cleaved by esterase activity or in acidic conditions, which results in release of galantamine.

WO 2014/016430 discloses transmucosal administration of benzgalantamine via intranasal, buccal or sublingual modes, in addition to various formulations and salts of benzgalantamine, including for example lactate, gluconate, maleate and saccharate salts. Further, nasal application of benzgalantamine in comparison to oral application of Galantamine was evaluated in a study by Baakman et al (2016). Therein, nasal application of benzgalantamine resulted a lower incidence of gastrointestinal adverse effects such as nausea and vomiting in comparison to oral administration of Galantamine. Reduced side effects of benzgalantamine in comparison to Galantamine were also observed in a multiple ascending dose study of benzgalantamine administered by intranasal application (Bakker et al., 2020). In terms of the daily dosing of benzgalantamine versus oral galantamine, benzgalantamine was well tolerated up to a twice daily dose of 22 mg showing a reduced incidence of GI side effects relative to a single 16 mg dose of oral galantamine. No gastrointestinal adverse events were observed at a twice daily dose of 11 mg benzgalantamine.

Often drug solutions or emulsions are used for transmucosal administration of drugs, such as via the nasal but also via the sublingual or buccal route. Thereby, the use of drug solutions has several disadvantages over solid dosage forms for oral application, including the need for a highly soluble drug to achieve effective single dose levels, as the volume that can be applied to the nasal or oral cavity in a single dosing event is limited. Further, often long-term stability issues of drug solutions occur, thus requiring for example reconstitution directly before administration or additional stabilizing and viscosity control agents within the solution. Salts of benzgalantamine and stability issues of their solutions are disclosed in WO 2014/016430. Highly concentrated solutions of benzgalantamine gluconate were metastable, with the salts converting to less-soluble stable salt forms upon storage, requiring subsequent heating of the solution and precautions for avoiding precipitation upon storage.

In comparison to drug solutions or suspensions, solid dosage forms for oral application such as tablets provide high stability and easier and straightforward manufacturing. However, the advantageous properties of the prodrug benzgalantamine over Galantamine, such as reduced gastrointestinal side effects due to pharmacological inactivity prior to cleavage, are typically difficult to obtain when administered orally as tablets. This is because the pro-drug benzgalantamine is an ester that has been found to be instable in acidic environments (such as exists in the stomach) and is cleaved enzymatically in many tissues. The cleavage of benzgalantamine results in the presence of Galantamine in the stomach, provoking gastrointestinal adverse effects. In general, the occurrence of adverse effects such as gastrointestinal adverse effects can reduce adherence to oral therapy. It is likely that adherence can be improved by reduced or less severe adverse effects.

It is known in the prior art that dosage forms for oral application such as tablets and capsules can be coated with an acid resistant, enteric coating, thereby preventing dissolution of the tablet or capsule in the acidic environment, and thus preventing release and cleavage of the drug in the stomach. The possibility of employing enteric coated tablets comprising benzgalantamine (ALPHA-1062) is disclosed in WO 2014/016430. However, no details are provided regarding particular formulations, excipients, methods of manufacture, pH values at which release is intended, or any reports of efficacy or potential side effects.

Despite the provision of various formulations of galantamine and benzgalantamine and salts thereof in the prior art, further developments are required for improved, more efficacious oral formulations for delivering galantamine to a subject, that are clinically effective and cause reduced side effects.

SUMMARY OF THE INVENTION

In light of the prior art, the technical problem underlying the invention was the provision of pharmaceutical compositions comprising benzgalantamine (ALPHA-1062) for oral administration that do not exhibit the disadvantages of the prior art.

One object of the invention was to provide improved or alternative means for pharmaceutical compositions comprising benzgalantamine for oral delivery, that show reduced adverse effects, in particular reduced gastrointestinal adverse effects, while showing high bioavailability.

Another object of the invention was to provide improved or alternative means for galantamine administration, that are clinically effective and show reduced adverse effects, in particular reduced gastrointestinal adverse effects, while showing high bioavailability. Considering that the active past of benzgalantamine is galantamine itself, one aim of the invention is to provide galantamine treatment via oral delivery without or with reduced unwanted side effects.

Another problem underlying the invention was the provision of oral solid dosage forms and formulations comprising benzgalantamine showing improved pharmacokinetic properties in comparison to the dosage forms and formulations disclosed in the prior art, thereby providing effective treatment of diseases and/or symptoms associated with cognitive impairment and/or cholinergic deficits while showing reduced adverse effects.

Another problem underlying the invention was the provision of oral solid dosage forms and formulations comprising benzgalantamine showing improved pharmacokinetic properties in comparison to the dosage forms and formulations disclosed in the prior art independent of the food and beverage intake of a subject.

These problems are solved by the features of the independent claims. Preferred embodiments of the present invention are provided by the dependent claims.

In one aspect, the invention relates to a pharmaceutical composition in the form of a tablet, said tablet comprising:
 a. a tablet core, wherein said core comprises benzgalantamine or salt thereof, and
 b. an enteric coating, wherein said enteric coating is configured for dissolution at pH 5.5 and above.

Surprisingly, the compositions of the present invention show excellent pharmacokinetic properties and treatment efficacy while showing a low incidence of adverse effects in a subject.

As benzgalantamine is an ester, which is instable in acidic environment in the stomach, and is cleaved enzymatically in many tissues, oral administration of benzgalantamine typically results in pro-drug cleavage and provoking gastrointestinal adverse effects due to the effect of galantamine in the stomach. Enteric coating of solid dosage forms for oral administration prevents release of benzgalantamine in the stomach and thus acidic or enzymatic cleavage.

The inventive composition, comprising an enteric coating dissolving at pH 5.5 and above, surprisingly shows an advantageous pharmacokinetic profile, while showing reduced gastrointestinal adverse events.

As shown in the examples below, the inventive composition results in a decreased maximum plasma concentration ($c_{max}$) of Galantamine while maintaining an area under the curve (AUC) of Galantamine in plasma comparable to an immediate release reference formulation of galantamine (without enteric coating).

Further, the inventive compositions result in an increased $c_{max}$ of Galantamine while maintaining an AUC comparable to RAZADYNE extended-release capsules.

The inventive compositions thus provide a benefit over the compositions known in the prior art, as adverse effects, in particular gastrointestinal adverse events, are reduced due to lower $c_{max}$ compared to immediate release formulations, while treatment efficacy is maintained due to increased $c_{max}$ over RAZADYNE extended-release capsules and similar AUC to the oral galantamine compositions known in the prior art.

Such beneficial effects of the inventive compositions, which is in particular achieved by the enteric coating configured to dissolve at pH 5.5 or above, could not have been expected by a person skilled in the art.

Due to the enteric coating of the inventive compositions, the release of benzgalantamine occurs in the intestine above pH 5.5, resulting in a slower and lower rise to $c_{max}$ of Galantamine compared to an immediate release composition, releasing galantamine in the stomach and a higher $c_{max}$ compared to an extended-release composition. Both the rate at which plasma concentrations of benzgalantamine increase, and the absolute concentration of benzgalantamine in plasma, influence the side effect profile and efficacy. The slower rise to $c_{max}$ and lower $c_{max}$ of the inventive composition compared to an immediate release formulation thus advantageously reduces side effects.

After release of benzgalantamine from the inventive compositions in the intestine, the drug is potentially subject to conversion to galantamine through esterase action in the compartments: (a) in the lumen of the intestine, (b) during its transport across the intestinal wall (Ho et al. 2017, Xu et al. 2015), and (c) exposed to esterase activity in (portal) blood (Rudakova et al. 2010).

The inventive composition however surprisingly does not provoke the side effect profile observed with immediate release formulations known in the prior art, even though benzgalantamine is completely or nearly completely converted to galantamine and only negligible (or below the limit of quantitation) amounts of benzgalantamine are detected in the blood stream after administration to a subject (see examples 2 and 3 below). This leads to the finding that the inventive composition surprisingly does not result in free galantamine concentrations in the gastrointestinal tract and intestinal wall that provoke gastrointestinal side effects observed for compositions of the prior art.

This represents a surprising and beneficial effect, as it would have been expected that conversion of benzgalantamine in compartments (a-c) after release in the intestine may have resulted in galantamine concentrations activating the enteric cholinergic nervous system, resulting in gastrointestinal adverse events such as nausea, vomiting, diarrhea. The inventive formulation thus advantageously provides protection against gastrointestinal adverse events, while achieving complete conversion of the prodrug to galantamine and a similar AUC compared to the immediate and extended-release reference formulations.

Further, without being bound to theory, the results of the examples below demonstrate that the rate at which the drug is presented to the liver for first pass metabolism, is such that it doesn't overwhelm its metabolic capacity in order to completely, or nearly completely, convert benzgalantamine to galantamine. This increases the safety profile and tolerability of the inventive compositions over compositions known in the prior art.

The compositions of the present invention thus enable a combination of beneficial features and properties that a skilled person would not have expected. Achieving a substantial reduction of gastrointestinal adverse effects while maintaining or and potentially enhancing treatment efficacy, in addition an increased safety profile, represents an unexpectedly beneficial tablet formulation that shows surprising advantages over formulations of the prior art and/or the expectations of a skilled person in the field of drug formulation. Thereby, the inventive enteric coated composition configured to dissolve at pH 5.5 advantageously enables treatment of patients who previously have discontinued treatment with AChE inhibitors due to intolerable gastrointestinal side effects associated with orally administered tablets.

In one embodiment, the enteric coating is configured for dissolution at pH 5.5 and above, such as at pH 5.5, 5.6, 5.7, 5.8, 5.9, 6, 6.1, 6.2, 6.3, 6.4, 6.5, 6.6, 6.7, 6.8, 6.9 or 7, or at values above 7.

In one embodiment, the enteric coating is configured for dissolution within a range of pH values formed from any two values disclosed herein. By way of example, in some embodiments, the enteric coating is configured for dissolution at pH 5.5 to 7, at pH 5.5 to 6.5, or pH 5.5 to 6.

In one embodiment, the enteric coating is a copolymer of methacrylic acid and ethyl acrylate.

In one embodiment, the copolymer comprises a ratio of carboxylic acid groups of methacrylic acid and ester groups of ethyl acrylate of 2:1 to 1:2, or about 1:1, and the average molecular weight of the copolymer is about 250 kDa.

In one embodiment, the copolymer comprises a ratio of carboxylic acid groups of methacrylic acid and ester groups of ethyl acrylate of 2:1 to 1:2, such as 2:1, 1.8:1, 1.6:1, 1.5:1, 1.4:1, 1.2:1, 1:1, 1:1.2, 1:1.4, 1:1.5, 1:1.6, 1:1.8 and 1:2.

In one embodiment, the enteric coating is or comprises Acryl-Eze II and/or Eudragit L 100-55.

By way of example, Acryl-Eze II and/or Eudragit L 100-55 are considered a gold standard for delayed release coatings for drug release in mid to upper small intestine, and reliably allow dissolution above pH 5.5. Eudragit products are typically available from Evonik Operations GmbH, Eudragit L 100-55 has a Cas-No of 25212-88-8, and a composition of methacrylic acid-ethyl acrylate copolymer (1:1). Acryl-EZE II is available in various pigmented formulations, is available from Colorcon, and employs Evonik's globally accepted enteric polymer Eudragit L 100-55.

In one embodiment, the tablet core comprises a water-soluble filler.

In one embodiment, the water-soluble filler is a sugar.

In one embodiment, the sugar is mannitol.

In one embodiment, the tablet core comprises a glidant.

In one embodiment, the glidant is colloidal silicon dioxide.

In one embodiment, the tablet core comprises one or more lubricants.

In one embodiment, the lubricant is sodium stearyl fumarate and/or magnesium stearate.

In one embodiment, the tablet core comprises sodium stearyl fumarate and magnesium stearate.

In one embodiment, the tablet core is coated by a film coating comprising hydroxypropyl methylcellulose (HPMC), wherein said film coating is in direct contact with the tablet core and is coated by the enteric coating.

In one embodiment, the film coating comprises HPMC and polyethylene glycol, preferably wherein the film coating is or comprises Opadry YS-1-7006.

In one embodiment, the benzgalantamine is present as a gluconate salt.

In one embodiment, the benzgalantamine gluconate salt is present as crystalline solid form A (anhydrous form). Reference is made to WO 2022/150917 (U.S. Ser. No. 11/795, 176B2), which is incorporated by reference in full, in which the crystalline solid form of benzgalantamine gluconate Form A is disclosed.

As described therein, polymorphic studies were conducted with benzgalantamine (ALPHA-1062) utilizing a variety of solvents and crystallization conditions (Table 5 of WO 2022/150917) and subsequent XRPD analyses. Seven unique crystalline materials were observed and isolated, and were designated as Forms A, B, C, D and Materials E, F and G (FIG. 6 of WO 2022/150917). Form A of benzgalantamine is an anhydrous crystalline material with concomitant melt/decomposition onset near 117° C. Based upon WO 2022/150917, anhydrous Form A, stored under appropriate temperature and humidity conditions to maintain its form and stability, appears best suited of the various benzgalantamine forms to be used in formulation and manufacture of drug products.

In one embodiment, the invention relates to a composition comprising a crystalline solid form of benzgalantamine gluconate (Form A), wherein said crystalline form has prominent peaks at 3.61, 10.98, 14.41 and 18.44 degrees 2-theta (±0.2) in a powder X-ray diffraction pattern. Although enteric coated formulations have been previously postulated, none of the prior art formulations have employed Form A. The use of Form A of benzgalantamine gluconate is in some embodiments advantageous due to its high stability during storage, maintaining both high chemical stability with none, low or negligible amounts of chemical impurities, and also stability of Form A itself, thus avoiding conversion to other forms or hydrates, and a high solubility, thereby also enabling the advantageous effects described herein.

In one embodiment, Form A has one or more additional prominent peaks at 15.20, 17.31, 17.79, 22.77, 23.64, 24.88 and 34.31 degrees 2-theta (±0.2) in a powder X-ray diffraction pattern.

These peaks are selected from the prominent peak list presented in WO 2022/150917 and appear to exhibit no substantial overlap with prominent peaks in the XRPD patterns for Forms B-D, or Materials E-G. In one embodiment, Form A has at least five prominent peaks selected from the list consisting of 3.61, 10.98, 13.80, 14.41, 14.56, 15.08, 15.20, 17.02, 17.31, 17.79, 18.44, 19.24, 20.18, 20.91, 21.22 and 22.40 degrees 2-theta (±0.2) in a powder X-ray diffraction pattern.

The use of Form A of benzgalantamine gluconate represents a preferred and advantageous embodiment of the invention, as stability of Form A can be maintained after formulation during storage. Form A can also enable high drug solubility and effective therapeutic effect.

As demonstrated within the examples below (example 5) the inventive compositions comprising benzgalantamine gluconate as crystalline solid form A (anhydrous form) possess high chemical and crystalline stability and advantageous dissolution properties even upon long term storage, also under accelerated conditions. No impurities or decomposition products were detected, showing high chemical stability of the API benzgalantamine within the inventive compositions.

Further, no changes in dissolution under acid stage and buffered stage were observed, when compared to the dissolution before storage, demonstrating no change in the crystalline form upon storage.

In one embodiment, the tablet core comprises:
Benzgalantamine or salt thereof in an amount (wt % of the tablet core) of 5-20%,
A water-soluble filler in an amount of 60-90%,
A glidant in an amount of 0.1-5%, and
One or more lubricants in an amount of 0.1-5%.
In one embodiment, the tablet core comprises:
Benzgalantamine or salt thereof in an amount (wt % of the tablet core) of 5-20%,
Mannitol in an amount of 60-90%,
Colloidal silicon dioxide in an amount of 0.1-5%,
Sodium stearyl fumarate in an amount of 0.1-5%, and
Magnesium stearate in an amount of 0.1-5%.

In one embodiment, the tablet core comprises:
Benzgalantamine or salt thereof in an amount (wt % of the tablet core) of 10-15%,
Mannitol in an amount of 70-90%,
Colloidal silicon dioxide in an amount of 0.5-2%,
Sodium stearyl fumarate in an amount of 1-4%, and
Magnesium stearate in an amount of 0.5-2%.

The above-mentioned formulations and embodiments disclose preferred amounts of each component. Variation in these amounts, or combinations of different ranges of each component from different embodiments, is envisaged.

In one embodiment, the enteric coating is present in an amount, determined by weight gain in % in addition to the tablet core, of 5-20%, preferably of 7-15%, more preferably about 8%, about 10%, about 12% or about 14%.

In one embodiment, the film coating is present in an amount, determined by weight gain in % in addition to the tablet core, of 2-10%, preferably about 3-7%, more preferably about 5%.

In one embodiment,
a. the tablet core comprises:
Benzgalantamine or salt thereof in an amount (wt % of the tablet core) of 10-15%,
Mannitol in an amount of 70-90%,
Colloidal silicon dioxide in an amount of 0.5-2%,
Sodium stearyl fumarate in an amount of 1-4%, and
Magnesium stearate in an amount of 0.5-2%, and
b. the enteric coating is present in an amount, determined by weight gain in % in addition to the tablet core, of 7-15%, and
c. a film coating is present in an amount, determined by weight gain in % in addition to the tablet core, of 3-7%, wherein said film coating is in direct contact with the tablet core and is coated by the enteric coating.

All values provided herein, for example the specific preferred values for each component, may vary by +/−2 wt %, or by +/−1 wt %. All values for each of the tablet components provided herein, may be used to characterize the invention independent of the presence or amount of any other component, or in combination with other components of the example compositions. The preferred range disclosed below for each component may be used to define the composition, either independent of other components or in combination with other components. These embodiments are not limited by total weight of the compositions, but in some embodiments by the wt % values of each component without limitation to absolute weight.

Embodiments relating to benzgalantamine (ALPHA-1062), 5 mg, 10 mg or 15 mg tablets:

| Component | Function | % wt | mg/tablet | | | Preferred rage % wt |
| --- | --- | --- | --- | --- | --- | --- |
| | | | 5 mg | 10 mg | 15 mg | |
| Tablet Core | | | | | | |
| Benzgalantamine (Galantamine Benzoate API; Gluconate Form A) | API | 12.692% | 7.506 | 15.012 | 22.516 | 5-20 |
| Mannitol | Water-soluble filler | 82.768% | 48.949 | 97.898 | 146.833 | 60-90 |
| Colloidal Silicon Dioxide | Glidant | 1.000% | 0.591 | 1.182 | 1.774 | 0.1-5 |
| Sodium Stearyl Fumarate | Lubricant | 2.540% | 1.502 | 3.004 | 4.506 | 0.1-5 |
| Magnesium Stearate | Lubricant | 1.000% | 0.591 | 1.182 | 1.774 | 0.1-5 |
| Total | | 100.000% | 59.140 | 118.280 | 177.403 | — |

-continued

| Component | | Function | % wt | 5 mg (mg/tablet) | 10 mg (mg/tablet) | 15 mg (mg/tablet) | Preferred rage % wt |
|---|---|---|---|---|---|---|---|
| Tablet Coating | | | | | | | |
| Opadry (seal) (sub-coating) | | Film Coating | 5% of tablet core | 2.957 | 5.914 | 8.870 | 2-10% of tablet core |
| Acryl-EZE II (enteric) | White/RM4123 | Enteric Coating | 10% of sub-coated tablet core | 6.210 | — | — | 2-10% of tablet core |
| | Grey/RM4131 | Enteric Coating | 7.5% of sub-coated tablet core | — | — | 13.970 | 2-10% of tablet core |
| | Purple/RM4130 | Enteric Coating | 9% of sub-coated tablet core | — | 11.178 | — | 2-10% of tablet core |
| Total | | | — | 68.306 | 135.372 | 200.244 | — |

In one embodiment, the composition is configured to release benzgalantamine after administration to a subject in the small intestine of said subject at pH 5.5 and above.

In one embodiment, the composition shows at most 10% dissolution of benzgalantamine in the dissolution test according to USP 711 under acidic stage (pH 1,2) after 120 minutes and at least 80% release of benzgalantamine in the dissolution test according to USP 711 under buffered stage (pH 5.5 or 6.8) after 60 minutes.

In one embodiment, the composition shows at most 10% dissolution of benzgalantamine in the dissolution test according to USP 711 under acidic stage (pH 1,2) after 120 minutes and/or at least 80% release of benzgalantamine in the dissolution test according to USP 711 under buffered stage (pH 5.5 or 6.8) after 60 minutes.

In one embodiment, the composition shows at most 5% dissolution of benzgalantamine in the dissolution test according to USP 711 under acidic stage (pH 1,2) after 120 minutes and at least 80% release of benzgalantamine in the dissolution test according to USP 711 under buffered stage (pH 5.5 or 6.8) after 45 minutes.

In one embodiment, the composition shows at most 5% dissolution of benzgalantamine in the dissolution test according to USP 711 under acidic stage (pH 1.2) after 120 minutes and/or at least 80% release of benzgalantamine in the dissolution test according to USP 711 under buffered stage (pH 5.5 or 6.8) after 45 minutes.

In one embodiment, the composition shows at most 10% dissolution of benzgalantamine in the dissolution test according to USP 711 under acidic stage (pH 1.2) and in the presence of 20% (v/v) or less ethyl alcohol after 90 minutes.

In one embodiment, the composition shows at most 5% dissolution of benzgalantamine in the dissolution test according to USP 711 under acidic stage (pH 1.2) and in the presence of 20% (v/v) or less ethyl alcohol after 90 minutes.

The inventive compositions surprisingly show no dissolution or dissolution of negligible amounts under acidic conditions even in the presence of up to 20% (v/v) ethyl alcohol. Further, the compositions show no change in the release profile under buffered conditions in the presence of up to 20% (v/v) ethyl alcohol. These results demonstrate that the dissolution properties and the release of benzgalantamine from the inventive composition advantageously is not influenced by the presence of alcohol, such as up to 20% (v/v) ethyl alcohol. Thus, the inventive compositions provide a high safety profile and advantageous pharmacokinetic properties even in the presence of alcohol, i.e., during alcohol intake of a subject the compositions are administered to.

In one embodiment, after administration of the composition to a subject, benzgalantamine is at negligible levels or below a lower limit of detection in the plasma of the subject (exhibits complete or nearly complete conversion of benzgalantamine to Galantamine).

This observation represents a surprising and beneficial effect obtained by the present formulation. Previous studies have observed that, for example when using nasal administration, that significant amounts of benzgalantamine, in some cases up to 10% of administered compound, were not cleaved to release galantamine and benzgalantamine could be observed in the blood of subjects who received the drug. The (near) complete cleavage of benzgalantamine to galantamine, as shown in the reports below regarding clinical study participants, enables a quick and complete release of active agent and surprisingly is not associated with adverse effects, as may have been expected when observing release of galantamine in the gastrointestinal tract.

In one embodiment, after administration of the composition to a subject,
  a. a lower maximal plasma concentration ($c_{max}$) of Galantamine is obtained compared to an immediate release galantamine reference composition, and
  b. an area under the plasma curve (AUC) of Galantamine is obtained at 80-125% of the AUC for the reference composition,
  c. wherein preferably said immediate release galantamine reference composition is a tablet comprising no coating or a coating configured for dissolution below pH 5.5 and a molar amount of Galantamine above the molar amount of galantamine in benzgalantamine in the pharmaceutical composition.

In one embodiment, after repeated administration of the composition to a subject,
  a. a greater maximal plasma concentration of Galantamine at steady state ($c_{max,ss}$) is obtained compared to an extended release galantamine reference composition, and
  b. an area under the plasma curve (AUC) of Galantamine is obtained at 80-125% of the AUC for the reference composition,
  c. wherein preferably said extended release galantamine reference composition (8 mg QD) is a solid dosage form configured for extended release of Galantamine and comprising a molar amount of Galantamine above the molar amount of galantamine in benzgalantamine (5 mg BID) in the pharmaceutical composition.

In one embodiment, after administration of the composition to a subject, the subject has a likelihood of having an adverse event related to the gastrointestinal tract of equal to or less than 2%, such as 2%, 1.8%, 1.6%, 1.4%, 1.2%. 1%, 0.8%, 0.6%, 0.4%, 0.2% and 0%.

Surprisingly the compositions of the present invention show excellent pharmacokinetic properties resulting in low incidence of adverse effects, in particular gastrointestinal adverse events, in a subject.

Thereby, gastrointestinal adverse events are reduced due to lower $c_{max}$ compared to immediate release formulations, while bioavailability is maintained due to increased $c_{max}$ over RAZADYNE extended-release capsules, and similar AUC to the oral galantamine compositions known in the prior art. Overall, the inventive composition provides enhanced tolerability and maintained bioavailability and can thus be considered as clinically more effective.

After release of benzgalantamine from the inventive compositions at pH 5.5 or above in the intestine, the drug is potentially subject to conversion to galantamine through esterase action in the intestine, during transport across the intestinal wall and in the (portal) blood. It could have thus been expected that conversion of benzgalantamine after release in the intestine would result in galantamine concentrations activating the enteric cholinergic nervous system, resulting in gastrointestinal adverse events such as nausea, vomiting, diarrhea. The inventive composition however beneficially does not result in free galantamine concentration in the gastrointestinal tract that provokes the side effect profile observed with immediate release formulations known in the prior art, even though benzgalantamine is completely or nearly completely converted to galantamine and no or only negligible amounts of benzgalantamine are detected in the blood stream after administration to a subject.

In one aspect, the invention relates to a pharmaceutical composition for use in the treatment of a brain disease associated with cognitive impairment and/or with a cholinergic deficit.

In a related aspect, the invention further relates to a method for the treatment of a brain disease associated with cognitive impairment and/or with a cholinergic deficit, comprising administering the pharmaceutical composition as described herein to a subject in need thereof.

In one embodiment, the brain disease is selected from the group consisting of a brain disease with a cholinergic deficit, Alzheimer's disease, Parkinson's disease, dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, poisoning, anesthesia, spinal cord disorders, central inflammatory disorders, Lewy Body Disease, multiple sclerosis, skeletal muscle pain, autism, Rett's syndrome, motor neuron disease such as amyotrophic lateral sclerosis, traumatic brain injury, post-traumatic stress disorder, postoperative delirium, neuropathic pain, abuse of alcohol and drugs, addictive alcohol and/or nicotine craving, severe gas in the gastro-intestinal tract (GIT), constipation, low blood pressure, erratic heart rate, and effects of radiotherapy.

In one aspect, the invention relates to a method for preparing a pharmaceutical composition in the form of a tablet according to any one of the preceding claims, wherein said composition is prepared by blending components of the tablet core to form a blend, compressing said blend to form a tablet core, coating said tablet core with a film coating and coating said film coating with an enteric coating.

The method for preparation of the composition of the present invention employs direct blending of the excipients, which are well mixable and show good flow properties when blended, allowing direct compression of the composition blend (also termed herein "blend").

It was unexpected and beneficial that direct compression could be employed for the formulation of tablets comprising high amounts of benzgalantamine and salts thereof such as benzgalantamine gluconate, preferably Form A. Only few active ingredients are suitable for direct compression and often require careful selection and high amounts of excipients to enable direct compression to a tablet. The method of the present invention enables a straightforward, cost-efficient, reliable, and high-throughput approach towards formulation of benzgalantamine tablets with high single dose levels for oral administration, which represents an improvement over alternative methods of production.

The features of the invention relating to the composition in form of a tablet comprising benzgalantamine as described herein, are relevant to and considered disclosed in combination with other aspects of the invention, such as the method for manufacturing the composition and the use for the treatment of a disease and/or symptoms associated with cognitive impairment and/or with a cholinergic deficit and vice versa. For example, the composition, methods for manufacture and use of said tablet are immediately relevant to the other aspects of the invention and may be used to characterize them appropriately, as understood by a skilled person.

DETAILED DESCRIPTION OF THE INVENTION

Galantamine ((4aS,6R,8aS)-3-Methoxy-11-methyl-4a,5,9,10,11,12-hexahydro-6H-benzofuro[3a,3,2-ef][2]benzazepin-6-ol (CAS 357-70-0)), is a reversible acetylcholinesterase inhibitor, (AchEI) and thus belongs to the group of reversible AchE inhibitors. It further enhances cholinergic activity by non-competitive, allosteric modulation of the nicotinic acetylcholine receptors (nAChR).

It is approved as immediate release tablet and oral solution and extended-release capsule and tablet and marketed as RAZADYNE® and RAZADYNE® ER (U.S.) and as REMINYL® (elsewhere).

The chemical structure of galantamine is:

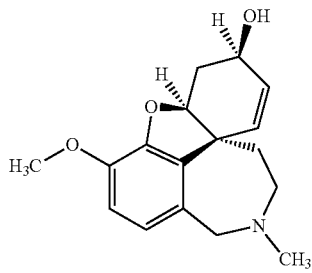

The chemical structure of benzgalantamine is:

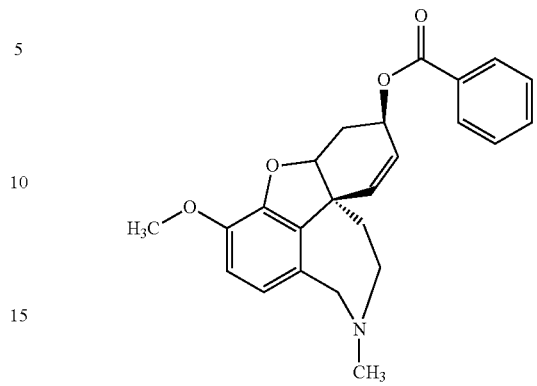

According to the full prescribing information of RAZADYNE® and RAZADYNE® ER (U.S.) and the, the regulatory approved indication is mild to moderate dementia of Alzheimer's type. According to the first approval of REMINYL in Sweden which was followed by several approvals in other European states the indication is similar to the U.S. approval for mild to moderate dementia of Alzheimer's type. RAZADYNE® tablets are available as 4 mg, 8 mg and 12 mg galantamine tablets. RAZADYNE® ER capsules are available as −8 mg, 16 mg and 24 mg extended-release capsules. The recommended initial dosage regime for RAZADYNE® 4 mg tablets is twice daily. This dose may be increased up to 12 mg twice daily. The recommended initial dose and dosage regime for RAZADYNE® ER capsules is one 8 mg capsule daily, which may be increased to 24 mg once daily.

Galantamine is well absorbed with an absolute oral bioavailability of ~90% and is rapidly and completely absorbed with a $t_{max}$ of ~1 hour. $C_{max}$ was decreased by 25% and $T_{max}$ was delayed by 1.5 hours, when galantamine was administered with food. The mean volume of distribution of galantamine is 175 L and plasma protein binding is 18% at therapeutic conditions. In whole blood, galantamine is mainly distributed into the cellular fraction (52.7%) (RAZADYNE®, 2020). Maximum inhibition of acetylcholinesterase activity of about 40% was achieved about 1 hour after a single oral dose of 8 mg galantamine in healthy male subjects (IB third edition, May 2020). Galantamine is metabolized by hepatic cytochrome P450 (CYP) enzymes, glucuronidated, and excreted unchanged in the urine. In vitro studies indicate that CYP2D6 and CYP3A4 were the major isoenzymes involved in the metabolism of galantamine, and inhibitors of both pathways increase oral BA of galantamine modestly.

Benzgalantamine, also termed ALPHA-1062 ((4aS,6R,8aS)-4a,5, 9,10,11,12-hexahydro-3-methoxy-11-methyl-6H[1]benzofuro[3a,3,2-ef][2]benzazepin-6 benzoate gluconate salt) (CAS. No.: 224169-27-1, also termed galantamine benzoate, memogain or GLN-1062) is a galantamine prodrug, exhibiting no pharmacological effect on aChE activity or cholinergic activity. It is cleaved by carboxylesterases and in acidic environment, releasing one molecule of galantamine from each molecule of prodrug Acetylcholine (ACh) is a transmitter of the nervous system acting on postsynaptic muscarinic acetylcholine (mAChR) or nicotinic acetylcholine receptors (nAChR). ACh is cleaved by acetylcholinesterase (aChE) present in the synaptic cleft, thus inhibition of aChE and thus cleavage of ACh, results in enhanced concentrations of ACh in the synaptic cleft. ACh is present in the central nervous system (CNS) and the peripheral nervous system (PNS). The PNS can be further subdivided into somatic nervous system and autonomic nervous system (parasympathetic nervous system, sympathetic nervous system, and enteric nervous system). In the somatic nervous system, ACh is a transmitter at the neuromuscular endplate. In addition, ACh occurs as a transmitter in preganglionic sympathetic and in all parasympathetic neurons, mediating signal transmission from the postganglionic-parasympathetic neurons to the end organs. Effects of ACh include mediation of contraction of skeletal muscle, regulation of the autonomic nervous system influencing for example blood pressure, heart rate, digestion and metabolism, and further regulation of reward and cognitive functions in the CNS. A deficiency of ACh (cholinergic deficit) can result in impairment of functions and effects of ACh in the somatic nervous system and autonomic nervous system and further in the CNS resulting in impairments of cognitive function (cognitive impairment), learning and memory.

Diseases and/or symptoms associated with cognitive impairment and/or with a cholinergic deficit include but are not limited to brain diseases with a cholinergic deficit, a brain disease with a cholinergic deficit, Alzheimer's disease, Parkinson's disease, dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, poisoning, anesthesia, spinal cord disorders, central inflammatory disorders, Lewy Body Disease, multiple sclerosis, skeletal muscle pain, autism, Rett's syndrome, motor neuron disease such as amyotrophic lateral sclerosis, traumatic brain injury, post-traumatic stress disorder, postoperative delirium, neuropathic pain, abuse of alcohol and drugs, addictive alcohol and/or nicotine craving, severe gas in the gastro-intestinal tract (GIT), constipation, low blood pressure, erratic heart rate, and effects of radiotherapy. These medical indications represent preferred embodiments of the medical use of the invention in the treatment of a disease and/or symptoms associated with cognitive impairment and/or with a cholinergic deficit.

"Administration" or "treatment," as it applies to an animal, human, experimental subject, cell, tissue, organ, or biological fluid, refers to contact of a pharmaceutical, therapeutic, diagnostic agent, compound, or composition to the animal, human, subject, cell, tissue, organ, or biological fluid. "Administration" and "treatment" can refer, e.g., to therapeutic, placebo, pharmacokinetic, diagnostic, research, and experimental methods. The term "subject" includes both human and veterinary subjects. "Treatment," as it applies to a human, veterinary, or research subject, refers to therapeutic treatment, prophylactic or preventative measures, to research and diagnostic applications.

The invention encompasses administration of an effective amount of chemical substance as described herein to a subject or patient in need thereof. "Effective amount" or "therapeutically effective amount" means an amount sufficient to elicit an appreciable biological response such as ameliorate a symptom or sign of a disorder or physiological condition when administered to a subject or patient. An effective amount for a particular patient or veterinary subject may vary depending on factors such as the condition being treated and the overall health and age of the patient. An effective amount can be the maximal dose or dosing protocol that avoids significant side effects or toxic effects. "Effective amount" also relates to an amount of the prodrug substance or pharmaceutical composition thereof, sufficient to allow or facilitate appreciable biological response such as the amelioration of a symptom or sign of a disorder, condition, or pathological state.

A prodrug is defined as inactive or less active agent that is transformed (also termed "metabolized") in an organism to an active agent also termed "metabolite". In this context, a prodrug is an inactive or less active precursor of an active drug that undergoes transformation into the active form of the drug in vivo by enzymatic cleavage or one or more non-enzymatic chemical processes in a predictable fashion. Prodrugs are developed to influence physicochemical, organoleptic, pharmacokinetic and pharmacodynamic properties of active drugs. Usually, prodrugs are characterized in that the drug is chemically coupled to a carrier molecule, which is cleaved off in the organism (carrier-bound prodrugs) resulting in transformation to the active drug. Common carrier-bound prodrugs comprise coupling of the carrier by a covalent ester linkage (ester prodrugs). Further types of prodrugs include bio precursors, which are not coupled to a carrier molecule but metabolized or conjugated directly in the organism resulting in the active drug, and co-prodrugs (mutual prodrugs), comprising two or more active drugs coupled to each other. The prodrug of the present invention benzgalantamine comprises a covalent ester linkage between the active drug galantamine and benzoate, which upon cleavage releases the active drug galantamine.

The present invention relates further to salts of benzgalantamine. In some embodiments, benzgalantamine is present as a salt of benzgalantamine, or is present in a crystalline form of benzgalantamine, or is present as a polymorph or hydrate of benzgalantamine. The terms "salt" refers to salts prepared by conventional means that include basic salts of inorganic and organic acids, including but not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, saccharate, succinate, tartrate, thiocyanate, tosylate and undecanoate. For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

In a preferred embodiment the salt comprises of stoichiometric and/or non-stoichiometric salts and/or hydrates of benzgalantamine, whereby the salt is preferably described as:

Benzgalantamine·n HX·m $H_2O$, whereby n, m=0-5 and n and m can be the same or different, and HX=an acid, selected preferably from acetic acid, citric acid, lactic acid, gluconic acid, maleic acid or saccharic acid.

Preferred are quaternary nitrogen salts (also termed "quaternary ammonium salts" herein) of benzgalantamine with gluconic acid (gluconate salt), acetic acid (acetate salt), maleic acid (maleate salt), lactic acid (lactate salt), citric acid (citrate salt), and saccharic acid (saccharate salt).

Salts of benzgalantamine disclosed in the prior art include maleate, lactate saccharate and gluconate. In one preferred embodiment of the invention the benzgalantamine or a salt thereof is benzgalantamine gluconate.

The chemical structure of benzgalantamine (ALPHA-1062) gluconate is:

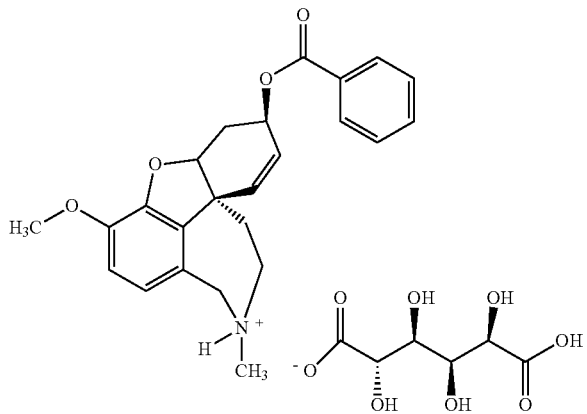

By way of example, the gluconate salt of benzgalantamine can be created according to the following established general scheme:

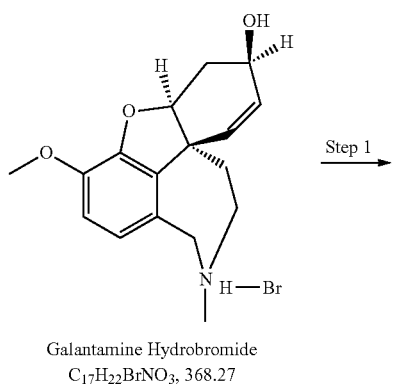

Galantamine Hydrobromide
$C_{17}H_{22}BrNO_3$, 368.27

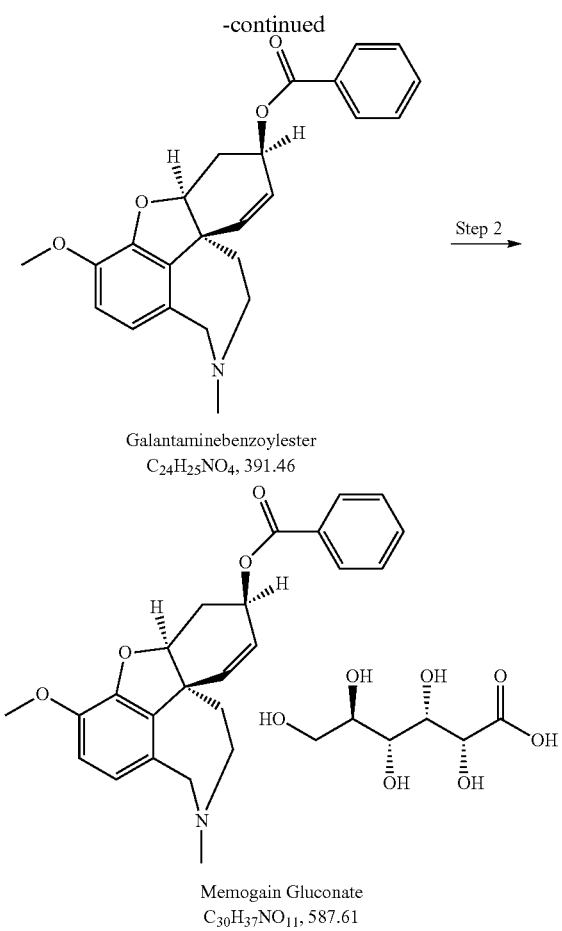

Galantaminebenzoylester
C₂₄H₂₅NO₄, 391.46

Memogain Gluconate
C₃₀H₃₇NO₁₁, 587.61

In one embodiment, the composition comprises a crystalline solid form of benzgalantamine gluconate (Form A), wherein said crystalline form has prominent peaks at 3.61, 10.98, 14.41 and 18.44 degrees 2-theta (±0.2) in a powder X-ray diffraction pattern. The use of Form A represents a preferred embodiment and may be combined with any one or more other embodiments or aspects of the present disclosure.

These 4 peaks are selected from the prominent peak list provided below and appear to exhibit no substantial overlap with prominent peaks in the XRPD patterns for Forms B-D, or Materials E-G, as disclosed in WO 2022/150917. In one embodiment, Form A can therefore be reliably distinguished using one or more prominent peaks, for example as mentioned above, upon comparison of the corresponding powder X-ray diffraction patterns. In one embodiment, the presence of these peaks in a powder X-ray diffraction pattern may be used to identify Form A and/or distinguish Form A from the solid forms described previously in the art, for example those described in WO2014/016430.

In one embodiment, Form A has one or more additional prominent peaks at 15.20, 17.31, 17.79, 22.77, 23.64, 24.88 and 34.31 degrees 2-theta (±0.2) in a powder X-ray diffraction pattern. These peaks are selected from the prominent peak list and appear to exhibit no substantial overlap with prominent peaks in the XRPD patterns for Forms B-D, or Materials E-G.

In one embodiment, Form A has at least five prominent peaks selected from the list consisting of 3.61, 10.98, 13.80, 14.41, 14.56, 15.08, 15.20, 17.02, 17.31, 17.79, 18.44, 19.24, 20.18, 20.91, 21.22 and 22.40 degrees 2-theta (±0.2) in a powder X-ray diffraction pattern.

Typically, not all peaks from this list need be detected in order to determine the presence of Form A in any given preparation. According to the invention, for example in some embodiments, 1, 2, 3, 4, 5, 6, 7, 8, 9, 10 or more peaks, preferably those with relatively high signal intensity, may be employed to determine any given crystal form. For example, the 4, 5, 6, 7, 8, 9 or 10 most intense peaks may be employed to identify any given crystal form. In one embodiment, sufficient identification of any given crystal form, such as Form A, is achieved when the presence of at least three or four prominent peaks can be determined based on XRPD comparisons.

Typically, prominent XRPD peaks are the strongest low angle, non-overlapping peaks observed in a XRPD pattern. In some embodiments, the "prominent peaks" have preferably a 20% relative intensity, preferably 30% relative intensity, more preferably 40% relative intensity, in a powder X-ray diffraction pattern. The values of relative intensity may however vary depending on device or analysis mode and are not inherently limiting to the solid forms described herein.

In one embodiment, Form A has peaks at 7.25 and/or 12.67 degrees 2-theta (±0.2) in a powder X-ray diffraction pattern. These peaks are of relatively low intensity compared to the peaks outlined above as predominant peaks. However, peaks at 7.25 and/or 12.67 degrees 2-theta appear to be absent in all other patterns for Forms B-D or Materials E-G.

In one embodiment, the peaks are determined using powder X-ray diffraction analysis in transmission mode.

In one embodiment, Form A has at least three peaks selected from the list consisting of 10.98, 14.41, 17.31, 18.44 and 22.40 degrees 2-theta (±0.2) in a powder X-ray diffraction pattern. In one embodiment, said three peaks are within the five peaks with the highest relative intensity in a powder X-ray diffraction pattern obtained using analysis in transmission mode. In one embodiment, these five peaks are the most intense peaks in the XRPD pattern using transmission mode, as outlined in the examples below.

In one embodiment, the peaks are determined using powder X-ray diffraction analysis in reflectance mode.

In one embodiment, Form A has at least three peaks selected from the list consisting of 3.61, 7.25, 10.98, 14.56 and 22.40 degrees 2-theta (±0.2) in a powder X-ray diffraction pattern. In one embodiment, said three peaks are preferably within the five peaks with the highest relative intensity in a powder X-ray diffraction pattern obtained using analysis in reflectance mode. In one embodiment, these five peaks are the most intense peaks in the XRPD pattern using reflectance mode, as outlined in the example below.

In one embodiment, Form A has one or more peaks selected from the list consisting of 3.61, 7.25, 10.98, 14.56, 22.40 degrees 2-theta (±0.2) in a powder X-ray diffraction pattern. These peaks are also observable from the XRPD pattern using reflectance mode.

In one embodiment, Form A has one or more doublets selected from the list consisting of 14.41 and 14.56, 15.08 and 15.20, and 24.88 and 25.09 degrees 2-theta (±0.2) in a powder X-ray diffraction pattern. These doublets may be used to identify Form A, and optionally distinguish the Form from other forms.

Provided below is a Table of the typically observed XRPD pattern peaks for Form A collected in transmission mode.

Peak list Form A: Peak list determined from the powder X-ray diffraction pattern of Form A, according to FIG. 8.

Accuracy of degrees 2-theta is provided at 2 decimal points, some variation dependent on batch or device may be evident.

| 2θ (°)  | d (Å) | I (%) |
|---------|-------|-------|
| 3.61*   | 24.5  | 47    |
| 7.25    | 12.2  | 18    |
| 10.52   | 8.40  | 14    |
| 10.98*  | 8.05  | 100   |
| 11.71   | 7.55  | 4     |
| 12.67   | 6.98  | 23    |
| 13.46   | 6.57  | 10    |
| 13.80*  | 6.41  | 45    |
| 14.41*  | 6.14  | 71    |
| 14.56*  | 6.08  | 52    |
| 15.08*  | 5.87  | 40    |
| 15.20*  | 5.82  | 46    |
| 16.16   | 5.48  | 25    |
| 16.44   | 5.39  | 22    |
| 17.02*  | 5.20  | 46    |
| 17.31*  | 5.12  | 66    |
| 17.79*  | 4.98  | 41    |
| 18.24   | 4.86  | 8     |
| 18.44*  | 4.81  | 67    |
| 19.24*  | 4.61  | 56    |
| 19.43   | 4.56  | 10    |
| 19.80   | 4.48  | 24    |
| 20.18*  | 4.40  | 40    |
| 20.91*  | 4.24  | 64    |
| 21.22*  | 4.18  | 57    |
| 21.54   | 4.12  | 19    |
| 22.09   | 4.02  | 19    |
| 22.40*  | 3.97  | 86    |
| 22.77*  | 3.90  | 41    |
| 23.64*  | 3.76  | 39    |
| 24.30   | 3.66  | 13    |
| 24.88*  | 3.58  | 41    |
| 25.09*  | 3.55  | 44    |
| 25.44   | 3.50  | 9     |
| 25.76   | 3.46  | 15    |
| 25.89   | 3.44  | 25    |
| 26.37   | 3.38  | 12    |
| 26.62   | 3.35  | 5     |
| 26.91   | 3.31  | 5     |
| 27.19   | 3.28  | 17    |
| 27.37   | 3.26  | 19    |
| 27.82   | 3.20  | 23    |
| 27.99   | 3.18  | 35    |
| 28.95   | 3.08  | 14    |
| 29.34   | 3.04  | 11    |
| 29.83   | 2.99  | 21    |
| 30.37   | 2.94  | 15    |
| 30.92   | 2.89  | 17    |
| 31.68   | 2.82  | 6     |
| 32.44   | 2.76  | 9     |
| 33.39   | 2.68  | 5     |
| 34.31   | 2.61  | 34    |

*Peaks may in some embodiments be considered as prominent peaks observed in the XRPD pattern.

In one embodiment, Form A exhibits an onset of melting at a temperature of 116-120° C., preferably at about 117° C., when assessed using differential scanning calorimetry (DSC).

In one embodiment, Form A exhibits a weight loss of <1%, preferably <0.5%, more preferably less than <0.3%, or <0.2%, prior to the onset of melt using DSC when assessed using Thermo-Gravimetric Analysis (TGA).

As used herein, crystalline preferably means a material that has an ordered, long range molecular structure. The degree of crystallinity of a crystal form can be determined by many techniques including, for example, powder X-ray diffraction, moisture sorption, differential scanning calorimetry, solution calorimetry, and dissolution properties.

Crystalline organic compounds consist of a large number of atoms that are arranged in a periodic array in three-dimensional space. The structural periodicity normally manifests distinct physical properties, such as sharp, explicit spectral features by most spectroscopic probes (e.g., X-ray diffraction, infrared and solid-state NMR). X-ray diffraction (XRD) is acknowledged to be one of the most sensitive methods to determine the crystallinity of solids. Crystals yield explicit diffraction maxima that arise at specific angles consistent with the lattice interplanar spacings, as predicted by Bragg's law. On the contrary, amorphous materials do not possess long-range order. They often retain additional volume between molecules, as in the liquid state. Amorphous solids normally unveil a featureless XRD pattern with broad, diffuse halos because of the absence of the long-range order of repeating crystal lattice.

Crystalline forms are preferred in many pharmaceutical applications. Crystalline forms are generally thermodynamically more stable than amorphous forms of the same substance. This thermodynamic stability is preferably reflected in the improved physical stability of the crystalline form. The regular packing of the molecules in the crystalline solid preferably denies the incorporation of chemical impurities. Hence crystalline materials generally possess higher chemical purity than their amorphous counterparts. The packing in the crystalline solid generally constrains the molecules to well defined lattice positions and reduces the molecular mobility that is the prerequisite for chemical reactions. Hence, crystalline solids, with very few notable exceptions, are chemically more stable than amorphous solids of the same molecular composition. Preferably, the crystalline forms of the benzgalantamine gluconate disclosed in the present application possess one or more of the advantageous chemical and/or physical properties disclosed herein.

As used herein, the term stable may relate to either chemical stability or to polymorph stability. Polymorph stability refers to the likelihood of a polymorph form remaining in its specific crystalline state under suitable storage conditions. For example, a stable polymorph form will maintain at least about 95% by weight, preferably at least about 98% by weight, and more preferably at least about 99% by weight or more of the crystalline form, in other words the form remains unchanged after storage under the indicated conditions for the indicated time. In the context of the present invention, Form A of the benzgalantamine gluconate appears to show good stability for example under conditions of storage at room temperature, and at low water activities, such at or under about 43% RH or of less than 0.12 aW, for multiple months. In some embodiments, Form A shows good chemical stability. In other words, benzgalantamine gluconate as Form A shows low, negligible or no conversion to distinct chemical structures, after storage under the appropriate conditions.

Powder X-ray diffraction (XRPD) measures the diffraction pattern of a crystalline material. Each active pharmaceutical ingredient (API) will produce a specific pattern depending on the structure of its crystal lattice. Each polymorph, pseudopolymorph, polymorph salt, or co-crystalline material will have its own specific pattern. For this reason, XRPD of an API can be carried out in controlled conditions to assess the presence or absence of crystalline material and any form conversions.

PXRD can also be used to determine if any change in crystalline form in the drug product has occurred during e.g. storage or stability studies. The identification of a crystalline form therefore relies on the presence of detectable diffraction peaks for any given crystalline form. In addition, the API peaks must be distinguishable from any crystalline excipient peaks, should a composition be assessed post-formulation. PXRD can also be used as a qualitative and sometime quantitative assessment of the degree of crystallinity of a pure API. A skilled person can assess PXRD patterns and identifying the presence and/or absence of suitable peaks that can be employed to characterize any given crystalline form of an API without undue effort.

In some embodiments, the peaks determined by a PXRD analysis are essentially the same as those presented in the examples below. The term "essentially the same" with reference to PXRD means that variabilities in peak positions and relative intensities of the peaks are to be taken into account. For example, a typical precision of the 2-Theta values is in the range of ±0.2° 2-Theta.

As used herein, characteristic XRPD peaks are a subset of the representative peaks from XRPD patterns of a crystalline form of a material that statistically can be proven to differentiate it from the other crystalline forms of that material. Not all crystalline polymorphs of a material necessarily have characteristic peaks.

As used herein, prominent XRPD peaks are typically the strongest low angle, non-overlapping peaks observed in the XRPD pattern. In some embodiments, the "prominent peaks" have preferably a 20% relative intensity, preferably 30% relative intensity, more preferably 40% relative intensity, in a powder X-ray diffraction pattern.

As used herein, representative XRPD Peaks are peaks from XRPD patterns of a crystalline form of a material that statistically show no bias from particle size/shape or preferred orientation during repeated samples and measurements.

As used herein, preferred orientation is phenomena observed in XRPD analyses where due to size/shape of the particles and the pattern collection technique employed it is very difficult or impossible to randomly orient the particles of the material during collection to achieve a pattern with statistically consistent intensities.

With respect to the relative intensities and the prominent peaks of the powder X-ray diffraction patterns mentioned above, the provided values of relative intensity are not intended as limiting for the identification of the prominent or characteristic peaks mentioned. As is known to a skilled person, the relative peak intensities will show some inter-apparatus variability, batch-to-batch variability, as well as variability due to degree of crystallinity, preferred orientation, sample preparation, and as such are provided as an indication and as a qualitative measure only, but not a limiting definition, of the intensities of the peaks in the powder X-ray diffraction patterns.

The term "prominent peak" in the context of defining the present invention is therefore not limited to the respective relative intensities provided above, and any one or more of the respective peaks may be determined as a prominent peak for any given form of benzgalantamine gluconate. Preferably at least 1, 2, 3 or 4 prominent peaks are used to characterize a crystalline form, in other embodiments, at least 5, 6, 7, 8 9 or 10 prominent peaks may be employed. A prominent peak is therefore also not limited to a peak unique to any given crystal form, rather the peak can, optionally in combination with a number of other peaks from the PXRD pattern, be used to identify a crystal form. In the context of the present invention, crystal Forms A-D may share multiple prominent peaks, but also exhibit peaks distinct from one another that can be used to differentiate between any two forms. In some embodiments, the prominent peaks mentioned in the embodiments of the invention may also be characteristic peaks and/or representative peaks.

The term "active ingredient" or "API" herein refers to a pharmaceutically active molecule as well as a pro-drug transformed to the pharmaceutically active molecule in the organism (e.g., benzgalantamine (ALPHA-1062)), and a pharmaceutically acceptable and/or therapeutically active salt thereof (e.g., benzgalantamine (ALPHA-1062) gluconate). The term further refers to pharmaceutically acceptable and therapeutically active hydrates, esters, amides, metabolites, enantiomers, polymorphs, analogs, etc. that induce a desired pharmacological or physiological effect or induce a desired pharmacological or physiological effect upon transformation to a pharmaceutically active molecule in the organism. Terms like "active agent", "active pharmaceutical ingredient", "drug substance", may be used synonymously for "active ingredient". The term "pharmaceutically active molecule" herein refers to a molecule that induces a desired pharmacological or physiological effect in an organism and/or subject. Terms like "active drug", "active molecule", "therapeutically active molecule", "therapeutically active drug", may be used synonymously for "pharmaceutically active molecule".

A "tablet" as used herein is considered a solid unit dosage form of a medicament comprising one or more excipients.

The term "excipient" means a pharmacologically inactive component such as a filler, lubricant, binder, disintegrant, glidant, flavoring agent, sweetener, colorant, film formers, gelling agent, acid regulator, preservative agent, absorption enhancers, stabilizing agent and the like, of a pharmaceutical product. The excipients that are useful in preparing a pharmaceutical composition are generally safe, non-toxic and are acceptable for veterinary as well as human pharmaceutical use. Reference to an excipient includes both one excipient and more than one excipient.

The excipients are described herein in some embodiments according to "wt %", or "percentage by weight" or "% by weight. The % wt values recited herein preferably relate to the percentage of material by weight present in the pharmaceutical composition in the form of a tablet.

According to the invention, a filler may be used as a bulking agent in tablets. Fillers used for tablets include but are not limited to sugars and sugar alcohols such as lactose, saccharose, glucose, mannitol, sorbitol, xylitol, and the like, oligo- and polysaccharides such as corn starch, rice starch, potato starch, wheat starch, modified starch derivatives, cellulose, microcrystalline cellulose (MCC), and the like, inorganic binders such as calcium phosphate, calcium hydrogen phosphate, calcium carbonate, and mixtures thereof.

According to embodiments of the invention, the preferred filler is mannitol. Mannitol (CAS No. 69-65-8) is a hexavalent sugar alcohol structurally derived from mannose and is naturally occurring among others in plants, algae and lichens. In the pharmaceutical industry mannitol is used as a filler, sweetener and binder. In the context of the invention mannitol is defined as a filler, preferably a water-soluble filler.

A glidant improves the flow properties of powder mixtures by reducing interparticle friction, so that the powder can flow better from the from the filling shoe into the die of the tablet press. Thus, flow regulators also improve the dosing accuracy. In particular, highly dispersed silicon dioxide such as colloidal silicon dioxide is used as a glidant.

Silicon dioxide is the oxide of silicon. It is a natural substance that occurs for example in crystalline in quartz, granite and sand, and is used in the manufacture of glass. In the pharmaceutical industry, various grades of silicon dioxide find wide application as excipients. Thereby in particular, highly dispersed silicon dioxide such as colloidal silicon dioxide is used as a glidant. The production of colloidal or highly dispersed silicon dioxide is carried out by flame hydrolysis from SiCl4 resulting in submicroscopic amorphous spheres of approx. 7-16 nm in diameter and an extremely large surface area of about 200 m2/g. Addition of low amounts of about 0.5% are usually sufficient to achieve substantially improved flow properties of powders.

A lubricant is an excipient added to facilitate the tableting process. Lubricants may facilitate flowability of a powder to easily fill in a die, may reduce friction between powder particles themselves and friction among a die, punch, granules and powder, and may facilitate tablet compressing and discharge from a die. Lubricants may thus prevent sticking of tablet compounds and tablets to tablet press punches and the die. Lubricants used for the formulation of tablets include magnesium stearate, calcium behenate, glycerol monostearate, stearic acid, sodium stearyl fumarate, talcum, hydrated vegetable fats such as hydrogenated castor oil, hydrogenated cottonseed oil and mixtures thereof. According to the invention, the one or more lubricants are preferably selected from the group consisting of sodium stearyl fumarate and magnesium stearate.

Sodium stearyl fumarate (CAS No. 4070-80-8) is synthetically produced by reacting stearyl alcohol with maleic anhydride. The product of this reaction then undergoes an isomerization step followed by salt formation to produce sodium stearyl fumarate. Sodium stearyl fumarate is used in oral pharmaceutical formulations as lubricant and is generally regarded as a nontoxic and nonirritant material.

Magnesium stearate (CAS No. 557-04-0) is the magnesium salt of stearic acid and belongs to the lime soaps. Magnesium stearate is a salt consisting of a magnesium ion (Mg2+) and two stearates. Magnesium stearate is water insoluble. It has a lamellar crystal structure resulting in reduction of the internal friction and a very small particle size of 3 to 15 µm. Thus, magnesium stearate is a well suited as lubricant as it is attaching to the surface of other particles in a powder mixture, reducing interparticular friction and friction with external surfaces.

In one embodiment the inventive composition may optionally comprise additional excipients such as a binder, a disintegrant and/or a flavoring agent.

A binder holds the ingredients in a tablet together and increases hardness and stability of a tablet. Binders are employed during granulation and for direct compression of tablets, ensuring that tablets and granules can be formed with required mechanical strength. Binders are preferably macromolecular polar amorphous substances that exhibit isotropic deformation behavior due to their amorphous nature and provide optimum conditions for pouring into any available cavity during compression. Binders for granulation act as processing aid during the granulation process. During direct compression of tablets binders are used to increase the cohesion of the powdery particles during compression, in order to obtain pharmaceutical forms with a defined hardness.

Binders can be classified into natural binders, semisynthetic polymer binders and synthetic polymer binders. In the context of the present invention the expression "natural binder" refers to a natural polymer binder, or a salt thereof or an inorganic binder including starches, processed or pretreated starches or starch salts, e.g., corn starch, potato starch, sodium starch, pregelatinized starch; alginic acid or salts thereof, e.g., sodium alginate; gelatin; Guar gum; gum Arabic; Candelilla wax; Carnauba wax, dextran, sugars and hexitols such as lactose, mannitol, saccharose and inorganic calcium compounds such as calcium hydrogen phosphate and tribasic calcium phosphate.

The expression "semisynthetic polymeric binder" refers to a chemical derivative of natural polymer binder, including chemical derivatives of cellulose or starch, preferably selected from the group consisting of hydrolyzed starches such as dextran and maltodextrin, hydroxypropyl cellulose (HPC, hyprollose), hydroxypropyl methyl cellulose (HPMC, Hypromellose), methyl cellulose (MC), hydroxypropyl cellulose (HPC, hyprollose), sodium carboxymethyl cellulose, and hydroxypropyl starch, microcrystalline cellulose (MC).

The expression "polymeric binder" refers to a fully chemically synthesized, non-natural polymer or co-polymer binder agent, preferably selected from the group of polyvinyl alcohol, polyvinyl caprolactam-polyvinyl acetate, polyethylene glycol (PEG), polyethylene glycol graft copolymer, and polyethylene glycol-polyvinyl alcohol graft copolymer (PEG-PVA), povidone (PVP), copovidone (COP), crospovidone (XPVP).

A disintegrant is an excipient used in tablets causing disintegration of the tablet, dissolution, and release of the active ingredient upon contact with moisture. Disintegrants can be classified into substances that increase capillarity, absorb moisture and swell, compounds which, when exposed to moisture flare up with gas evolution and substances that increase the wettability of the tablets (hydrophilizing agents).

Substances increasing capillarity include soy polysaccharides, alginic acid, crosslinked alginic acid, calcium alginate, natrium alginate, starches such as corn starch, pretreated starches such as pregelatinized starch, sodium carboxymethyl cellulose, crosslinked sodium carboxymethyl cellulose, sodium carboxymethyl starch, crosslinked sodium carboxymethyl starch, sodium starch glycolate, polyvinylpyrrolidone and crosslinked polyvinylpyrrolidone. Significant for the effect of this group is the exerted swelling pressure, the porosity and wettability of the tablet influencing the penetration of water into the tablet, which is a prerequisite for the disintegration process. These disintegrants are highly effective if they have high swellability, high swelling pressure and form a pore system in the tablet with sufficient wettability.

Highly effective disintegrants, which are more effective at much lower concentrations with greater disintegrating efficiency and mechanical strength compared with other disintegrants, are referred to as superdisintegrants. Superdisintegrants include soy polysaccharides, crosslinked alginic acid, sodium carboxymethyl cellulose, crosslinked sodium carboxymethyl cellulose, sodium carboxymethyl starch, crosslinked sodium carboxymethyl starch, sodium starch glycolate, polyvinylpyrrolidone and crosslinked polyvinylpyrrolidone. These water-insoluble substances have a high swelling capacity as well as a high capillary activity and ensure spontaneous and complete disintegration without slime formation.

Compounds which, when exposed to moisture flare up with gas evolution include sodium hydrogen carbonate and hydrogen carbonate in combination with citric acid or tartaric acid. Tablets with such a disintegrant disintegrate rapidly due to carbon dioxide evolution upon an acid reaction. These disintegrants are commonly used for oral tablets or effervescent tablets.

Hydrophilizing agents include sodium lauryl sulfate, polysorbate, highly dispersed silicon dioxide and microcrystalline cellulose (MCC). The representatives of this group are technically not considered as disintegrants themselves.

They rather enable disintegrants to become optimally effective. The tableting of lipophilic substances often causes considerable difficulties, since the wettability of such tablets is low, so that the incorporated disintegrants have no effect or only a very delayed effect. The addition of surface-active substances that hydrophilize the tablets/hydrophilizing agents) ensure penetration of water into the tablet and act on the incorporated disintegrants.

To correct the taste, flavoring agents as well as sweeteners such as sugar, sugar substitutes and sugar replacements can optionally be added to the inventive compositions. The taste receptors of the tongue can distinguish between the following tastes: sweet—sour—bitter—salty—umami. The basic taste of a drug can be harmonized by adding flavoring agents or sweeteners of the same or similar taste direction (e.g., sour taste with lemon) or covered with the opposite taste direction (e.g., bitter taste with vanilla). Because of its instability to hydrolysis in the presence of acidic active ingredients and its caries-promoting and calorie-providing effect, sugar (sucrose) as a sweetener is increasingly replaced by sweeteners, such as fructose, sorbitol, mannitol, xylitol, cyclamate, saccharin, or aspartame.

Methods for preparation of tablets include direct tableting (direct compression) and granulation including wet and dry granulation followed by compression. Tablet compression is carried out by a tablet press, which is a high-speed mechanical device. Two types of tablet presses are mainly used including eccentric presses and rotary presses. Both have two movable punches per functional unit (lower and upper punch), a die, and a hopper. These types of presses and their use are known to a person skilled in the art. According to the present invention direct compression is preferred.

In most cases, it is necessary to granulate the active ingredients and excipients before tableting, i.e., to convert the powder particles into granules. This results in a product with a larger particle size, which, compared to powder particles, has a better flowability. This ensures a continuous, uniform filling of the die of the tablet machine resulting in a constant tablet mass and high dosing accuracy. A granule is an asymmetric aggregate of powder particles that normally does not have a harmonious geometric shape and has an uneven, jagged or roughened surface resulting in good compressibility. Techniques for preparation of granulates include wet and dry granulation and are known to a person skilled in the art.

Direct tableting is the compression of powdered active ingredients or mixtures of active ingredients and excipients. According to embodiments of the invention, a powder or powder blend also termed "composition blend" or "blend" herein is compressed, which is a substantially dry solid, composed of preferably a large number of fine particles that may flow when shaken or tilted.

Direct tableting is characterized by a low workload and is thus more economical than the compression of granules, which requires the preceding steps of granulation before tablet compression. Direct tableting is further particularly advantageous for the processing of moisture- and heat-sensitive active ingredients whose stability is at risk during granulation operations.

However not all active ingredients and excipients are suitable for direct compression as cohesion forces between the blend particles might be not sufficient for formation of tablets with sufficient hardness or powder flow properties impede direct processing of the composition blend. By the addition of excipients such as binders, glidants, lubricants powder blends which are suitable for direct tableting can be obtained. Further, a good miscibility of the excipients and the active ingredients is a prerequisite for direct tableting. Powder mixtures tend to segregate e.g., due to different sizes and densities of excipient and active ingredient particles. The homogeneity of the mixture must be ensured during all process steps.

Tablet coating is a process by which an essentially dry, outer layer of coating material is applied to the surface of a dosage form such as a tablet. Typically tablet coating involves the application of a sugar or polymeric coat on the tablet. The advantages of tablet coating may relate to one or more of taste masking, odor masking, physical and chemical protection or control of release profile. There are two main methods usually applied for coating of pharmaceutical dosage forms: drum coating and fluidized bed coating. Drum coating is usually employed for coating of large, non-fluidizable particles such as tablets and capsules. Whereas drum coating may also be employed for coating pellets. A person skilled in the art is capable of choosing a suitable coating method with respect to the dosage form and coating agent.

For immediate-release tablets, a film coating is applied, which does not change the dissolution profile of core tablets significantly. The film coating is usually applied for better visual differentiation by color of different tablet strengths in order to avoid medication errors, and for improving the patient acceptance, e.g. easier swallowing. As disclosed in the US FDA guidance "Size, Shape, and Other Physical Attributes of Generic Tablets and Capsules" (dated Jun. 18, 2015), the presence of a coating can potentially affect the ease of swallowing tablets. The lack of a film coating can also decrease or prevent tablet mobility and increase esophageal transit times compared with a coated tablet of the same size and shape. Coating also can affect other factors that contribute to patient acceptance, such as palatability and smell.

A film coating may also serve as a basis (also termed sub-coating) for one or more further coatings to be applied on top of the film coating such as an enteric coating and/or a top-coating. A sub-coating may prevent interaction of the active ingredient with the additional coating such as the enteric coating. Materials ("coating agents") for film coating are known to a skilled person and comprise, without limitation, hydroxypropyl methyl cellulose (HPMC, hypromellose), polyethylene glycol (PEG, Macrogol), copovidone, povidone, polyvinyl alcohol and/or methacrylate polymers such as Eudragit E100. Besides a polymer a film coating may comprise further excipients including without limitation a plasticizer, a colorant, and/or an opacifier.

An "enteric coating" prevents dissolution or disintegration of a tablet in the acidic environment of the stomach. An enteric coating is usually applied for protecting a drug from degradation at acidic pH and by enzymes present in the stomach. Enteric coating may further prevent adverse effects associated with the dissolution of drugs in the stomach. Further, enteric coating may be configured to dissolve at a certain pH to control release of a drug from a tablet within the gastrointestinal tract. In one embodiment the enteric coating is configured to dissolve at pH 5.5 or above. In one embodiment the enteric coating is configured to release benzgalantamine in the small intestine of a subject at pH 5.5 and above. Materials for enteric coating are known to a skilled person and comprise, without limitation poly(meth) acrylate polymer such as a copolymer of methacrylic acid and ethyl acrylate, cellulose acetate phthalate (CAP), cellulose acetate succinate, hydroxypropyl methylcellulose phthalate, hydroxypropyl methylcellulose acetate succinate, polyvinyl acetate phthalate (PVAP), shellack, cellulose acetate trimellitate and/or sodium alginate.

Eudragit L-55 is an anionic copolymer of methacrylic acid and ethyl acrylate in an acid-ester ratio of about 1:1. The polymer is soluble at pH 5.5 or above. The polymer is commercially available as Eudragit L 30 D-55 (30% aqueous dispersion), Eudragit L 100-55 (powder) or Acryl-Eze II. Upon administration to a subject, a drug undergoes several effects and processes referred to as pharmacokinetics of the drug. The totality of all effects and processes influencing an active ingredient in an organism or subject is referred to as the LADME model, including liberation after administration, absorption also termed "resorption" herein, distribution, metabolism and excretion of the drug and its metabolites.

Liberation is the release of the active ingredient from the dosage form after administration, i.e., the conversion into a resorbable, dissolved form. The liberation of a drug is influenced by the pharmaceutical composition and excipients used therein. Liberation of the drug from sublingual and buccal tablets for administration in the oral cavity usually occurs fast due to short disintegration times of the tablets.

Absorption is the subsequent uptake of the drug through biological membranes, such as gastrointestinal mucosa, muscle tissue, into the bloodstream or lymphatic system. The absorption of a drug is dependent on the size of the absorption site, contact time and blood perfusion of the application site and further the physicochemical properties of the drug such as lipophilicity. The oral mucosa is well perfused, often resulting in a rapid onset of action and high blood levels of a drug. However, a balance must be found between good dissolution of the drug, which may be hindered in the case of highly lipophilic drug, and good absorption by the lipophilic mucosa, which is promoted by the lipophilicity of the drug.

The distribution of a drug refers to the transport of substances between different body fluids and tissues and is dependent on for example vascular permeability, perfusion rate of the tissue, pH value of the tissue, the blood brain barrier and the plasma protein and tissue binding ability of the drug and its lipophilicity.

A drug is subject to biochemical conversion and degradation processes at various sites in the body, the totality of which is referred to as metabolism or biotransformation. The first-pass effect thereby describes the proportion of substance metabolized during the first passage through the gut and liver.

The excretion of a drug or its metabolites from the bloodstream occurs largely via the kidneys and urine (renal excretion). A small proportion is excreted via the bile into the small intestine and subsequently in the stool. Of minor importance is excretion via skin (sweat) or mucosa (intestinal mucosa, intestinal excretion), as well as via the lungs (pulmonary excretion).

Important parameters describing the pharmacokinetics of a drug include the time of maximum concentration in the plasma ($t_{max}$), the half-life in plasma ($t_{1/2}$), the maximum concentration in plasma ($c_{max}$), the area under the curve (AUC), the distribution volume and the clearance.

For the characterization of absorption and for the estimation of bioequivalence of generic drugs, often the maximal plasma concentration ($c_{max}$) and the time to reach the $c_{max}$ ($t_{max}$) are reported. $T_{max}$ is proportional to the absorption velocity and independent of the dose, providing information about the velocity of drug absorption thus allowing conclusions to be drawn about the expected time of onset of the effect. $c_{max}$ is proportional to the administered dose and provides information about extent and velocity of drug absorption. If there is a direct correlation between plasma levels of the drug and the effect of the drug, $c_{max}$ gives an indication of the intensity of the effect. In addition, it can be assessed whether the plasma concentrations are within the therapeutically acceptable range.

The Area under the curve (AUC) refers to the area under the concentration-time curve (usually plasma level curve). It is a measure of the total amount of substance absorbed thus describing the systemically available amount of drug. The elimination half-life (plasma half-life, $t_{1/2}$) is the time during which the plasma concentration drops to half of the original value. According to the half-lives drugs can be divided into short-, medium- and long and long-acting drugs. The AUC can be calculated by several methods, including the trapezoidal rule and compartmental data analysis. These calculation methods are known to a person skilled in the art.

The Bioavailability of a drug is defined as the rate and extent to which the drug or active ingredient is absorbed from a dosage form and is present in the systemic circulation and/or at the site of action. The absolute bioavailability thereby describes the extent to which the active ingredient from a dosage form is systemically available compared to an intravenous solution of the active ingredient. The absolute bioavailability is determined by the physicochemical properties of the drug, the dosage form, and the physiological conditions at the absorption site. Relative bioavailability describes the extent and rate at which the active ingredient from a dosage form is systemically available compared to a reference dosage form applied by the same administration route. The relative bioavailability is usually determined by the dosage form.

BRIEF DESCRIPTION OF THE DRAWINGS

The invention is demonstrated by way of the figures disclosed herein. The figures provide support for a detailed description of potentially preferred, non-limiting embodiments of the invention.

EXAMPLES

Figure 1:
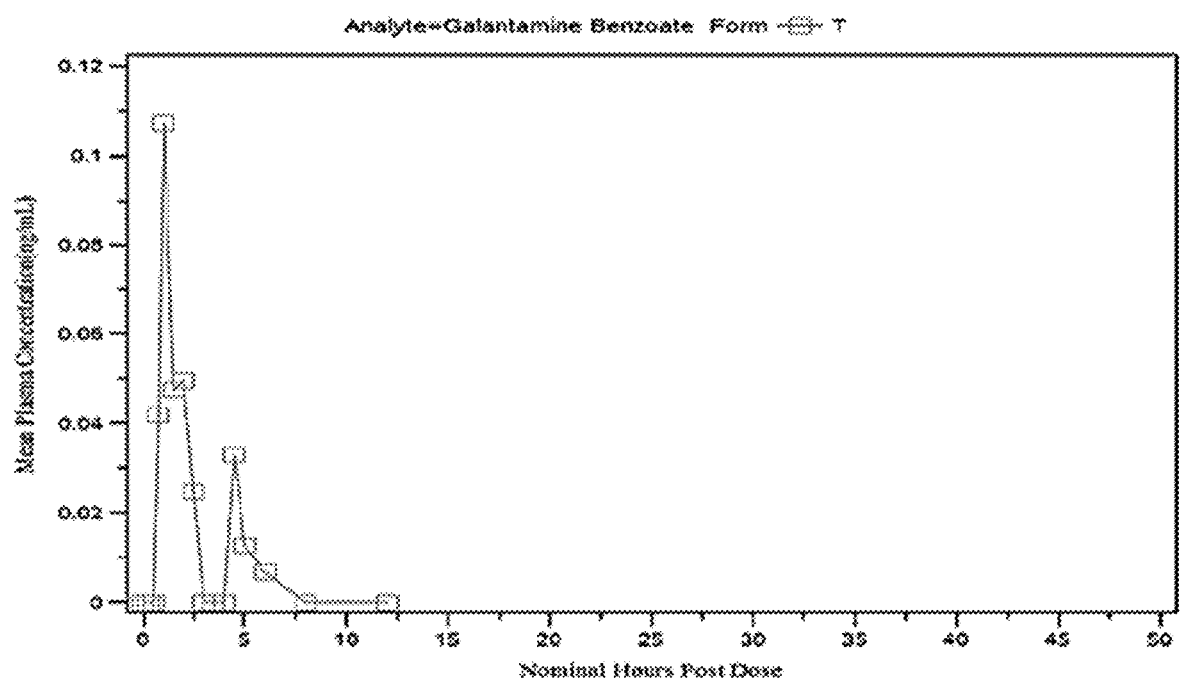
FIG. 1: Mean plasma benzgalantamine concentrations vs. Time Plots-Linear Scale. Clinical study evaluating inventive Galantamine Benzoate (benzgalantamine, ALPHA-1062) delayed release 5 mg tablet (T) vs. Galantamine Hydrobromide 4 mg tablet (R).

The invention is demonstrated by way of the examples disclosed herein. The examples provide technical support for a detailed description of potentially preferred, non-limiting embodiments of the invention.

Example 1: Inventive Compositions

General Procedure for the Preparation of Compositions by a Direct Compression Process:

Step-1 (Blending):
  I. The API (benzgalantamine (ALPHA-1062) gluconate Form A) is milled.
  II. A glidant and a first portion of a filler are blended with the API and subsequently de lumped through a mesh.
  III. A second portion of the filler is de lumped through a mesh and blended with the -mixture of step II.
  IV. One or more lubricants are de lumped through a mesh and blended with the mixture of step III.

Step-2 (Compression):
The blend from Step-1 IV is compressed into tablets by a compression machine using suitable machine parameters and suitable tooling.

Step-3 (Sub-Coating):
  I. A 7.5% suspension of a film former in purified water is prepared.
  II. The tablets of step-2 are charged into a coating pan and warmed until a bed temperature of 50° C. is obtained.
  III. The suspension of step I. is sprayed onto the tablets.
  IV. Once the target weight of coating is achieved, spraying is stopped, and the tablets are allowed to cool until a bed temperature of <30° C. is reached.

Step-4 (Enteric Coating):
  I. A 20% suspension of a film former for enteric coating is prepared in purified water.
  II. The sub-coated tablets of step-3 are charged into a coating pan and warmed until a bed temperature of 33° C. is obtained.
  III. The suspension of step I. is sprayed onto the tablets.
  IV. Once the target weight of coating is achieved, spraying is stopped, and the tablets are allowed to cool until a bed temperature of <30° C. is reached.

Inventive Examples

TABLE 1

Inventive benzgalantamine Delayed Release Tablet Formulations (5 mg, 10 mg, 15 mg)

| Component | % w/w | 5 mg | 10 mg | 15 mg |
|---|---|---|---|---|
| | | | mg/tablet | |
| Tablet Core | | | | |
| Benzgalantamine Gluconate API (GLN-1062 Gluconate Form A) | 12.692% | 7.506 | 15.012 | 22.516 |
| Mannitol (Pearlitol 200SD) | 82.768% | 48.949 | 97.898 | 146.833 |
| Colloidal Silicon Dioxide (CaboSil M5P) | 1.000% | 0.591 | 1.182 | 1.774 |

TABLE 1-continued

Inventive benzgalantamine Delayed Release Tablet Formulations (5 mg, 10 mg, 15 mg)

| Component | | % w/w | 5 mg | 10 mg | 15 mg |
|---|---|---|---|---|---|
| | | | | mg/tablet | |
| Sodium Stearyl Fumarate (PRUV) | | 2.540% | 1.502 | 3.004 | 4.506 |
| Magnesium Stearate | | 1.000% | 0.591 | 1.182 | 1.774 |
| Total | | 100.000% | 59.140 | 118.280 | 177.403 |
| Tablet Coating | | | | | |
| Opadry (seal) (sub-coating) | | 5% of tablet core | 2.957 | 5.914 | 8.870 |
| Acryl-EZE II (enteric) | White | 10% of sub-coated tablet core | 6.210 | — | — |
| | Grey | 7.5% of sub-coated tablet core | — | — | 13.970 |
| | Purple | 9% of sub-coated tablet core | — | 11.178 | — |
| Total | | — | 68.306 | 135.372 | 200.244 |

Dissolution Studies:

Methodology:

ALPHA-1062 (benzgalantamine) Delayed Release tablets are tested by two stage dissolution, first in acidic stage followed by buffer stage. The dissolution is conducted as per the USP <711> method using Apparatus I with 1000 ml of dissolution media of 0.01 N Hydrochloric acid or phosphate buffer pH 5.5 or 6.8, at temperature of 37.0±0.5° C., with basket rotation of 50 RPM. The duration of dissolution testing is 2 hours in acid stage and 75 minutes in buffer stage.

Results

TABLE 2a

Dissolution data for benzgalantamine (ALPHA-1062) delayed release tablet 5 mg

| Vessel | % dissolved (acidic stage) 120 min | % dissolved (buffer stage) | | | | |
|---|---|---|---|---|---|---|
| | | 15 min | 30 min | 45 min | 60 min | 120 min |
| 1 | 0 | 0 | 59 | 92 | 97 | 97 |
| 2 | 0 | 0 | 79 | 94 | 94 | 95 |
| 3 | 0 | 1 | 71 | 97 | 99 | 99 |
| 4 | 0 | 0 | 78 | 98 | 98 | 99 |
| 5 | 0 | 0 | 71 | 94 | 97 | 97 |
| 6 | 0 | 1 | 71 | 95 | 96 | 96 |
| Mean (6) | 0 | 1 | 71 | 95 | 97 | 97 |
| % RSD | — | 90.4 | 10.1 | 2.1 | 1.8 | 1.8 |

TABLE 2b

Dissolution data for benzgalantamine (ALPHA-1062) delayed release tablet 10 mg

| Vessel | % dissolved (acidic stage) 120 min | % dissolved (buffer stage) | | | | |
|---|---|---|---|---|---|---|
| | | 15 min | 30 min | 45 min | 60 min | 120 min |
| 1 | 0 | 0 | 46 | 95 | 96 | 96 |
| 2 | 0 | 0 | 60 | 93 | 94 | 94 |
| 3 | 0 | 0 | 22 | 93 | 97 | 97 |
| 4 | 0 | 0 | 71 | 93 | 96 | 98 |
| 5 | 0 | 0 | 40 | 92 | 95 | 95 |
| 6 | 0 | 0 | 53 | 94 | 97 | 97 |
| Mean (6) | 0 | 0 | 49 | 93 | 96 | 96 |
| % RSD | 0.0 | 0.0 | 34.9 | 1.2 | 1.2 | 1.3 |

TABLE 2c

Dissolution data for benzgalantamine (ALPHA-1062) delayed release tablet 15 mg

| Vessel | % dissolved (acidic stage) 120 min | % dissolved (buffer stage) | | | | |
|---|---|---|---|---|---|---|
| | | 15 min | 30 min | 45 min | 60 min | 120 min |
| 1 | 0 | 0 | 42 | 89 | 102 | 103 |
| 2 | 0 | 1 | 59 | 89 | 103 | 103 |
| 3 | 0 | 0 | 46 | 91 | 101 | 102 |
| 4 | 0 | 5 | 61 | 92 | 105 | 106 |
| 5 | 0 | 0 | 47 | 91 | 101 | 101 |
| 6 | 0 | 0 | 31 | 81 | 102 | 103 |
| Mean (6) | 0 | 1 | 47 | 89 | 102 | 103 |
| % RSD | 0.0 | 19.4 | 23.5 | 4.5 | 1.6 | 1.4 |

The inventive compositions comprising (5 mg, 10 mg or 15 mg benzgalantamine) show no release of benzgalantamine under acidic conditions (pH 1.2). Under buffered conditions (pH 6.8) >80% of benzgalantamine is released after 60 minutes. These results confirm that the inventive formulations do not release benzgalantamine under acidic conditions such as in the stomach, but release benzgalantamine at pH 5.5 and above such as at pH 6.8. This confirms the advantageous dissolution and release properties of the inventive compositions resulting in a reduced incidence of adverse effects, in particular gastrointestinal adverse effects, such as nausea and vomiting, and advantageous pharmacokinetic profile in a subject the composition is administered to.

Content Uniformity:
Methodology:

Content uniformity is determined as per USP <905>, each of ten tablets are individually weighed, dissolved in acidified buffer solution with mechanical shaking followed by sonication with acetonitrile and water (50:50) and then filtered. The aliquot of filtrate is diluted with water and analyzed by HPLC to determine the drug percent.

Results

TABLE 3 content uniformity of inventive compositions in %.

| Sample | Benzgalantamine (ALPHA-1062) delayed release tablet 5 mg | Benzgalantamine (ALPHA-1062) delayed release tablet 10 mg | Benzgalantamine (ALPHA-1062) delayed release tablet 15 mg |
|---|---|---|---|
| 1 | 93.0 | 96.8 | 100.0 |
| 2 | 99.3 | 100.3 | 100.1 |
| 3 | 101.5 | 100.5 | 98.7 |
| 4 | 96.9 | 100.9 | 99.2 |
| 5 | 96.8 | 99.2 | 99.0 |
| 6 | 95.6 | 98.6 | 101.5 |
| 7 | 95.8 | 100.2 | 99.8 |
| 8 | 95.3 | 96.9 | 99.5 |
| 9 | 95.9 | 97.6 | 97.4 |
| 10 | 95.3 | 103.0 | 101.6 |
| Mean (10) | 96.5 | 99.4 | 99.7 |
| % RSD | 2.4 | 2.0 | 1.3 |
| AV | 7.6 | 4.7 | 3.0 |

The inventive compositions (5 mg, 10 mg and 15 mg benzgalantamine) show a content uniformity >96%. These results demonstrate that the inventive composition can be produced in a reliable and reproducible manner independent of the dosage strength.

Example 2: Clinical Study (Benzgalantamine (APLPHA-1062) Delayed Release 5 mg Tablet Compared to Galantamine Hydrobromide (Yabao) 4 mg Tablet)

An open label, balanced, randomized, single oral dose, two-treatment, two-period two-way crossover study to evaluate the relative bioavailability (BA) of Benzgalantamine (ALPHA-1062) Delayed Release (OR) 5 mg Tablet compared to a Galantamine Hydrobromide 4 mg Tablet in healthy adult subjects under fasting conditions.

Test treatment (T): Benzgalantamine (ALPHA-1062) Tablet 5 mg according to the present invention.

Reference treatment (R): Galantamine Hydrobromide 4 mg tablet.

Objectives

Primary: Evaluation of relative bioavailability (BA) of an inventive single-dose of benzgalantamine (ALPHA-1062) 5 mg tablet (test) compared to a galantamine hydrobromide 4 mg tablet (reference) under fasting conditions.

Secondary: Evaluation of the safety and tolerability of single-dose administration of the inventive benzgalantamine (ALPHA-1062) tablet under fasting conditions.

Methodology:

Male and female study participants (in equal proportions) were enrolled in the study. A total of 54 normal, healthy, adult, human study participants were enrolled. All subjects either received test product (test) or reference product (reference) in each period according to the randomization schedule after ensuring maintenance of pre-dose restrictions (fasting for 10 hours prior to administration in sitting posture with 240±2 mL of drinking water at ambient temperature).

A washout period of 7 days was observed between both study periods. Study restrictions with respect to fluid intake and sitting positions were implemented during the restriction periods throughout the study in all periods. The total duration of participation for each subject was approximately 31 days including screening and washout period.

Study participants were instructed not to break, cut, and chew the tablet (test or reference) but to swallow whole and were asked to take it with the specified quantity of water. Water intake was not allowed for 1 hour before dosing until 1 hour after dosing except while administration of the dose. After dosing, the participants remained in sitting position for first two hours. On dosing days, meals were given as per the following schedule. Meals were the same for all study participants in all the periods.

TABLE 4

Schedule of standardized meals

| Day | Breakfast | Lunch | Snacks | Dinner |
|---|---|---|---|---|
| D − 1 | — | — | — | 11 hours pre dose |
| Dosing day (D) | — | 4 hours post dose | 8 hours post dose | 12 hours post dose |
| D + 1 | 24 hours post dose | 28 hours post dose | 32 hours post dose | 36 hours post dose |

Post dose meals were uniform in all the clinical periods and served at the same time in each study period. Study participants not meeting the requirement of 10 hours fasting prior to dosing were not eligible for dosing and discontinued from the study. No meals were provided for at least 4 hours post dose.

Study Participants:

54 study participants were enrolled, among them 38 participants were found eligible for the study. Healthy adult human male and female participants between 18-70 years of age with a body mass index between $\leq 18.0$ kg/m$^2$ and $\leq 30.0$ kg/m$^2$ at the screening visit were enrolled.

Further Study Activities:

Presentation and obtaining of informed consent form, urine drug screening including alcohol, vitals, physical examination, Columbia—Suicide Severity Rating Scale (C-SSRS) assessment, serum pregnancy test (only for female study participants), Covid Rapid Antigen test, body and baggage search, maintenance of pre-dose restrictions and provision of uniform diet were performed on check in day. A blood sample for evaluation of CYP2D6 Genotype was collected during Period-I check in only. Body weight (kg) was recorded at the time of check-in (only in period-I) and at the time of post study. Electrocardiogram (ECG) was measured within 24 hours prior to dosing of each period i.e., at the time of check-in and at 3 & 36 hours post dose (±60 minutes) and at the time of post study assessment.

Drug dispensing procedure was done under yellow monochromatic light conditions.

TABLE 5

Investigational Products, Dose, Mode of Administration and Lot/Batch Number:

| Test Product: T (test) | Reference Product: R (reference) |
|---|---|
| Benzgalantamine (gluconate Form A) delayed release tablet 5 mg | Galantamine Tablets USP 4 mg* (*Each tablet contains: Galantamine hydrobromide USP equivalent to 4 mg galantamine.) |
| Manufactured for: ALPHA Cognition, Inc. | Distributed by: State Run Pharmaceuticals, LLC Columbus, Ohio 43215 |
| Dose and Mode of Administration: Single oral dose. | Dose and Mode of Administration: Single oral dose. |
| Storage conditions: 20 to 25° C. (68° to 77° F.); excursions permitted between 15-30° C. (59°-86° F.) | Storage conditions: at 25° C. (77° F.); excursions permitted to 15 to 30° C. (59-86° F.) |

Pharmacokinetic Blood Sampling:

A total of 20 blood sampling time points were collected including pre-dose (0 hour) and post-dose samples in each period. In each period, 2 samples of pre-dose (each 5 mL) was collected within 1 hour prior to drug administration, to check for interference from contaminants or endogenous components at the retention time of peaks of interest and to analyze for lack of measurable drug concentrations by adding internal standard (ISTD).

Post dose samples were collected at 0.25, 0.5, 0.75, 1, 1.5, 2, 2.5, 3, 3.5, 4, 4.5, 5, 6, 8, 12, 16, 24, 36 and 48 hours post-dose. For pharmacokinetics (PK) of benzgalantamine (Only for Test Product (test)) post dose samples (each 5 mL) collected at 0.25, 0.5, 0.75, 1, 1.5, 2, 2.5, 3, 3.5, 4, 4.5, 5, 6, 8 and 12 hours were considered. For PK of Galantamine (for both test and reference) post dose samples (each 5 mL) collected at 0.25, 0.5, 0.75, 1, 1.5, 2, 2.5, 3, 3.5, 4, 4.5, 5, 6, 8, 12, 16, 24, 36 and 48 hours were considered.

The total volume of blood collected per study participant in this study did not exceed 255 mL for male and 259 mL for female including 9 mL for screening, 7-9 mL for post clinical assessment of lab parameters and 18 mL for discarding saline mixed blood sample resulting from use of intravenous cannula for 24 hours and an additional 2-9 mL which may be collected for repeat/additional lab tests, if required. Blood samples were collected by means of intravenous cannula until 24 hours post dose and the remaining blood samples were collected by means of direct, sterile venipuncture using pre-labelled 5 mL $K_2$EDTA vacutainers.

After collection, the blood samples were placed in wet ice bath condition maintained at approximately below 15° C. Once blood samples from all the study participants at each time point were available, they were centrifuged at 3800 rpm for 10 minutes at 10° C.±2° C. for separating the plasma. Centrifugation of all samples was done within 45 minutes after each sample draw time point. All plasma samples were separated and divided into two aliquots i.e. 1 mL in aliquot #1 and remaining plasma in aliquot #2 in properly labeled polypropylene tubes and immediately stored at −20° C.±4° C. until completion of analysis. After the analysis the plasma samples were retained for a duration of 90 days from the date of report submission to the sponsor or as per the sponsor requirement. The time from sample collection to placement in the freezer did not exceed 120 minutes. Plasma samples were analyzed for benzgalantamine (ALPHA-1062) and Galantamine using LC-MS/MS analysis. All the clinical activities were performed under yellow monochromatic light conditions.

Pharmacokinetic Analysis:

Pharmacokinetic parameters were calculated for benzgalantamine (ALPHA-1062) and Galantamine in plasma using Phoenix®® WinNonlin® 8.0 or higher version (Pharsight Corporation, USA) or SAS® 9.4 with Enterprise Guide 7.1 or higher version.

Primary parameters: $C_{max}$, $AUC_{0-t}$ and $AUC_{0-\infty}$.

| | |
|---|---|
| $C_{max}$ | Maximum measured plasma concentration over the time span specified. |
| $AUC_{0-t}$ | The area under the plasma concentration versus time curve from time '0' to the last measurable concentration, as calculated by the linear trapezoidal method. |
| $AUC_{0-\infty}$ | The area under the plasma concentration versus time curve from time '0' extrapolated infinity. $AUC_{0-\infty}$ was calculated as the sum of the $AUC_{0-t}$ plus the ratio of the last measurable concentration to the elimination rate constant |

Secondary parameters: $T_{max}$, $k_{el}$, $AUC_{0-t}$ $AUC_{0-\infty}$, AUC % extrap, $t_{1/2}$, $T_{lagg}$, Vz/F and Cl/F.

| | |
|---|---|
| AUC % extrap | Percent of $AUC_{0-\infty}$ extrapolated, represented as $(1 - AUC_{0-t}/AUC_{0-inf}) * 100$. |
| $T_{max}$ | Time of the maximum measured plasma concentration. If the maximum value occurs at more than one time point, $T_{max}$ is defined as the first time point of $C_{max}$. |
| $K_{el}$ | Apparent first-order elimination or terminal rate constant calculated from a semi-log plot of the plasma concentration versus time curve. The parameter was calculated by linear least-square regression analysis using the last three (or more) non-zero plasma concentrations of the terminal phase. |
| $t_{1/2}$ | The terminal half-life was calculated as $0.693/k_{el}$ |
| $AUC_{0-t}/AUC_{0-\infty}$ | The ratio of $AUC_{0-t}$ and $AUC_{0-\infty}$. |
| Apparent clearance (CL/F) | The steady state con- centration is determined only by clearance for any given dose rate. This is true if the bioavailability (F) of a dose is assumed to be 100% or equivalently, that clearance is the apparent clearance (CL/F) when the ratio of clearance to bioavailability is assumed to be constant. |
| Apparent volume of distribution (Vz/F) | A ratio of the total amount of drug in the body to the plasma concentration of the drugs |
| $T_{lag}$ | Time delay between drug administration and first observed concentration above LOQ in plasma. |

No value of $k_{el}$, $t_{1/2}$ and $AUC_{0-\infty}$ were reported for cases that do not exhibit a terminal log-linear phase in the concentration versus time profile. The actual post-dose time of collection was used in the calculation of the above pharmacokinetic parameters. Drug concentrations that are below limit of quantification (BLQ) were treated as "zero" in all pharmacokinetic and statistical calculations.

Gastrointestinal Adverse Events:

The safety assessments performed during the study included monitoring of gastrointestinal adverse events. Adverse event (AE) monitoring was done throughout the course of the study by clinical examination, vitals check, and participant observation of well-being, monitored throughout the study.

Statistical Analysis & Descriptive Statistics:

Statistical analysis was performed on pharmacokinetic data of samples assayed and quantified for Benzgalantamine and Galantamine in plasma. The statistical analysis was conducted on logarithmically (natural) transformed pharmacokinetic parameters using SAS® 9.4 with Enterprise Guide version 7.1 for Windows (SAS Institute Inc., Cary, NC, USA). The descriptive statistics (such as count (N), mean, median, minimum, maximum, standard deviation (SD) and coefficient of variation (CV) for the relevant pharmacokinetic parameters were estimated for both the tests and reference formulations. The geometric mean and coefficient of variation were estimated for $C_{max}$, $AUC_{0-t}$ and $AUC_{0-\infty}$. In this study, inferential statistics linear regression model was used.

Assessment of Bioavailability:

Assessment of bioavailability was done on the basis of the 90% confidence intervals of the differences of Geometric least squares treatment means for Ln-transformed $C_{max}$, $AUC_{0-t}$ and $AUC_{0-\infty}$ of Galantamine obtained after single-dose administration under fasting conditions. The acceptance criteria for bioavailability are that the entire confidence intervals for the difference of means of Ln-transformed $C_{max}$, $AUC_{0-t}$ and $AUC_{0-\infty}$ should fall within 80%-125%.

Determination of Sample Size

A total of 36 normal healthy adult, male or female study participants (in equal proportions) were dosed in the study.

T/R ratio=90%-111%

Expected Intra-Subject C.V (%)~18%

Significance Level=5%

Power=80%

Bioequivalence Limits=80-125%

Based on the above estimate, a sample size of 36 study participants were sufficient to establish bioequivalence between two formulations with adequate power, considering 10% dropouts due to adverse events or non-compliance or due to personal reasons.

Results

Demographics and Other Baseline Characteristics

TABLE 6

Demographics summary of all participants within the study (N = 34).

| Parameters | Age (yrs) | Weight (kg) | Height (cms) | BMI (kg/m$^2$) |
|---|---|---|---|---|
| Mean (SD) | 36.0 (8.00) | 66.9 (8.80) | 159.9 (8.95) | 26.1 (2.51) |
| Median | 35.5 | 66.9 | 158.1 | 26.3 |
| CV % | 22.2 | 13.2 | 5.6 | 9.6 |
| Range | (24.0, 57.0) | (48.8, 83.3) | (145.0, 175.0) | (20.8, 29.9) |

Treatment Compliance

All the study participants ingested the study drug; this was confirmed by direct observation of administration of study drug as well as by performing hand and mouth checks and further ascertained by the presence of plasma Benzgalantamine (ALPHA-1062) and Galantamine concentrations in individual blood samples following drug administration.

Pharmacokinetic Results

The pharmacokinetic parameters were calculated by linear mixed effects model. The pharmacokinetic parameters were statistically analyzed to compare the Test and Reference Products in regard to $C_{max}$, $AUG_{0-t}$ and $AUC_{0-\infty}$.

Figure 2:
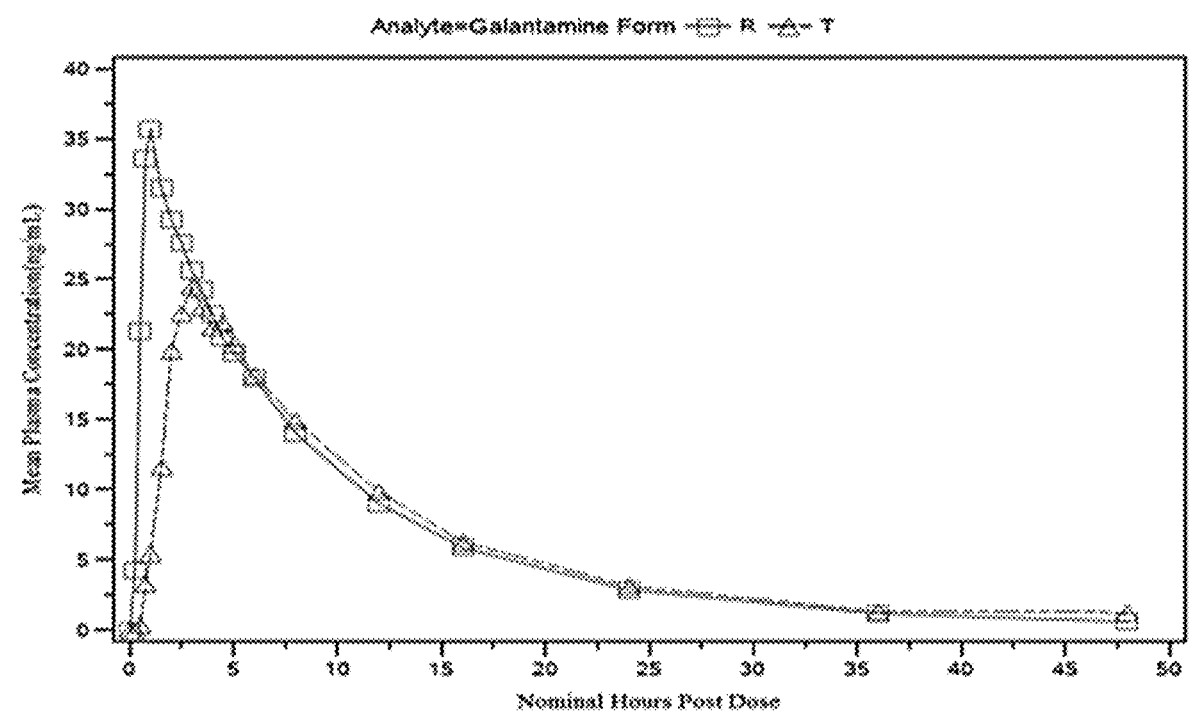
FIG. 2: Mean Plasma Galantamine concentrations Vs. Time Plots-Linear Scale. Clinical study evaluating inventive benzgalantamine delayed release tablet 5 mg tablet (T) vs. Galantamine Hydrobromide 4 mg tablet (R).
Figure 3:
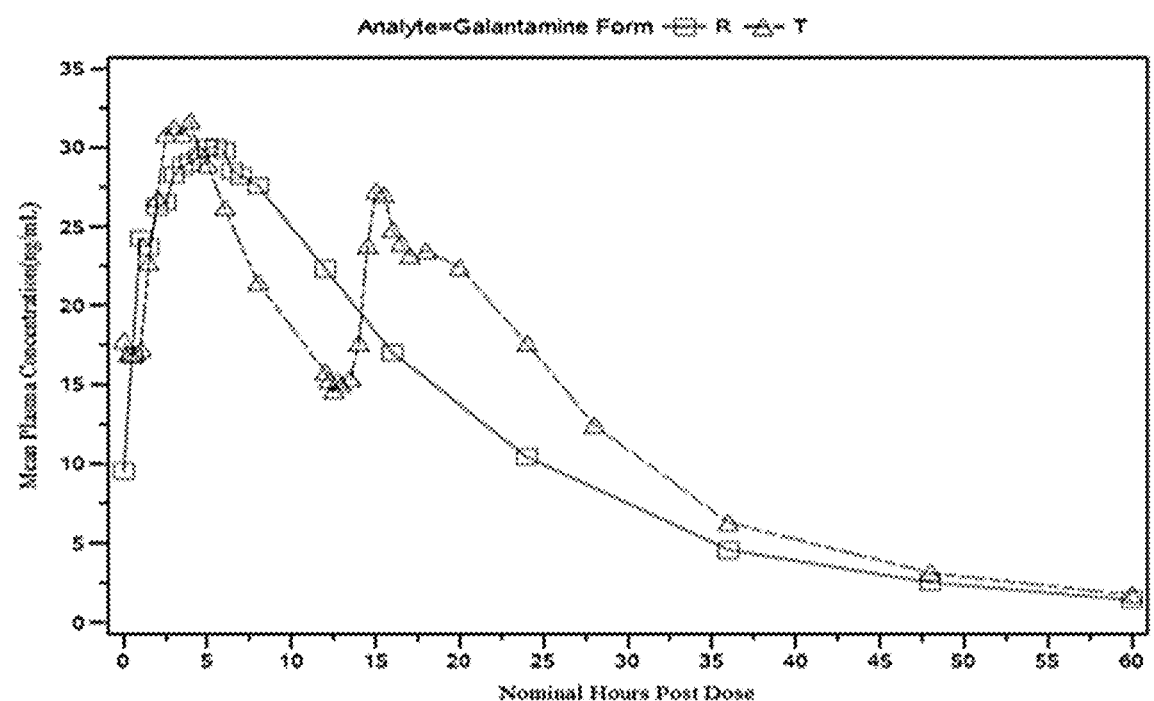
FIG. 3: Mean plasma Galantamine concentrations Vs. Time Plots-Linear Scale. Clinical study evaluating inventive benzgalantamine delayed-release tablets, 5 mg vs. Razadyne® ER (galantamine extended-release capsules) 8 mg.

The mean plasma concentration versus scheduled time plots (linear and log-linear scales) for Galantamine were obtained and are presented in FIGS. 2 and 3.

TABLE 7a

Arithmetic Mean (SD) of Pharmacokinetic Parameters of Galantamine.

| PK Parameter (Units) | Galantamine | | | |
|---|---|---|---|---|
| | N | Treatment T (Test) | N | Treatment R (Reference) |
| $C_{max}$ (ng/ml) | 34 | 31.461 (7.6143) | 34 | 41.126 (8.0053) |
| $AUC_{0-t}$ (ng · hr/mL) | 34 | 293.983 (61.0105) | 34 | 319.675 (64.9361) |
| $AUC_{0-\infty}$ (ng · hr/mL) | 34 | 324.509 (156.0687) | 34 | 328.256 (68.8577) |
| *$T_{max}$ (hr) | 34 | 2.50 (0.75, 5.03) | 34 | 1.00 (0.50, 2.50) |
| Kel (1/hr) | 34 | 0.074 (0.0166) | 34 | 0.078 (0.0151) |
| $t_{1/2}$ (hr) | 34 | 9.942 (2.8841) | 34 | 9.223 (1.7701) |
| AUC Ratio (%) | 34 | 95.181 (10.5765) | 34 | 97.503 (1.2155) |
| AUC_%extrap_obs# (%) | 34 | 4.819 (10.5765) | 34 | 2.497 (1.2155) |
| $T_{lag}$ (hr) | 34 | 1.08 (0.741) | 34 | 0.04 (0.093) |
| Vz_F_obs (mL) | . | NE | . | NE |
| Cl_F_obs (mL/hr) | . | NE | . | NE |

*For $T_{max}$, Median (Min, Max) are presented.

NE: Not Estimated.

TABLE 7b

Arithmetic Mean (SD) of Pharmacokinetic Parameters of benzgalantamine (ALPHA-1062).

| PK Parameter (Units) | N | Benzgalantamine Treatment T (Test) |
|---|---|---|
| $C_{max}$ (ng/ml) | 34 | 0.174 (0.3372) |
| $AUC_{0-t}$ (ng · hr/mL) | 9 | 0.439 (0.3552) |
| $AUC_{0-\infty}$ (ng · hr/mL) | 0 | NE |
| *$T_{max}$ (hr) | 34 | 0.00 (0.00, 4.50) |
| Kel (1/hr) | 0 | NE |
| $t_{1/2}$ (hr) | 0 | NE |
| AUC Ratio (%) | 0 | NE |
| AUC_%extrap_obs# (%) | 0 | NE |
| $T_{lag}$ (hr) | 9 | 1.53 (1.433) |
| Vz_F_obs (mL) | | NE |
| Cl_F_obs (mL/hr) | | NE |

*For $T_{max}$, Median (Min, Max) are presented.
NE: Not Estimated.

TABLE 8

Analysis of Variance for Galantamine (test (T) Vs reference (R))

| | P-Value | | |
|---|---|---|---|
| PK Parameter | Sequence | Period | Treatment |
| $C_{max}$ (ng/ml) | 0.1667 | 0.7538 | <.0001 |
| $AUC_{0-t}$ (ng · hr/mL) | 0.8333 | 0.2420 | 0.0003 |
| $AUC_{0-\infty}$ (ng · hr/mL) | 0.8719 | 0.2060 | 0.2969 |

TABLE 9

Statistical analysis results for the assessment of bioequivalence of Galantamine under fasting conditions.

| PK Parameter | Geometric Means | | Ratio % | CV | 90% Confidence Interval |
|---|---|---|---|---|---|
| | Test | Reference | | | |
| | Ln-Transformed: | | | | |
| $C_{max}$ (ng/ml) | 30.6791 | 40.4968 | 75.76 | 19.83 | (69.87, 82.14) |
| $AUC_{0-t}$ (ng · hr/mL) | 288.4345 | 313.4687 | 92.01 | 8.37 | (88.90, 95.23) |
| $AUC_{0-\infty}$ (ng · hr/mL) | 306.8242 | 321.4596 | 95.45 | 18.23 | (88.60, 102.82) |

The geometric mean (GM) Ratio with 90% CI of Ratio galantamine estimates of $C_{max}$, $AUC_{0-t}$ and $AUC_{0-\infty}$ values of the Benzgalantamine Delayed Release (DR) Tablet 5 mg (test) over those of the Galantamine Hydrobromide 4 mg tablet (reference) were 75.76 (69.87, 82.14), 92.01 (88.90, 95.23) and 95.45 (88.60, 102.82) respectively (Table 9). The 90% confidence interval (CI) for $C_{max}$ was not within 80-125% range for Galantamine. The 90% CI for $AUC_{0-t}$ and $AUC_{0-\infty}$ were within 80-125% range for Galantamine (Table 9).

$AUC_{0-t}$ and elimination related parameters ($AUC_{0-\infty}$, $AUC_{extrapolation}$, $K_{el}$ and $T_{1/2}$) for benzgalantamine (AL-PHA-1062) have not been estimated due to insufficiently measurable concentration profile (i.e., almost all values are zero or below limit of quantification (BLQ) at all times) (Table 7b). So, the maximum concentrations ($C_{max}$ points) were also observed to be zero. Therefore ln (0) is not mathematically predictable, so statistical analysis is performed after applying the transformed log.

Gastrointestinal Adverse Events

Adverse event monitoring in the form of clinical examination, vitals check and participant well-being was monitored during the study. The reported results were normal which concludes that all treatments were well tolerated and found to be safe.

TABLE 10

Incidence of gastrointestinal adverse events.

| | Reported Incidence by Treatment Groups Fasting Bioequivalence Study | |
|---|---|---|
| Body System/ Adverse Event | Test Treatment (test, T) | Reference Treatment (reference, R) |
| | Gastro Intestinal Disorders | |
| Vomiting | — | 1 (2.78%) |
| Diarrhea | — | 1 (2.78%) |
| Total | 0 (0%) | 2 (5.56%) |

N = Number of subjects with incidence of adverse events (AEs).
% = Percentage of the adverse event calculated by total number of study subjects that participated in the study.

A total of 2 gastrointestinal adverse events (AE) were reported. Of these 2 AE, 1 AE (i.e., vomiting) was reported during period-I, 1 AE (i.e., diarrhea) was reported during period-II. No Serious Adverse Events, Significant Adverse Events or deaths occurred in this study.

Overall subjects who were administered the inventive compositions showed a lower incidence of gastrointestinal adverse events in comparison to the benzgalantamine 4 mg tablet (reference) (Table 10). This demonstrates that the inventive composition comprising benzgalantamine and an enteric coating configured for dissolution at pH 5.5 or above shows an advantageous dissolution and release profile and improved pharmacokinetic properties in comparison to the reference composition comprising benzgalantamine and no such enteric coating, advantageously resulting in a reduced incidence of gastrointestinal adverse events.

CONCLUSION

Overall, the inventive compositions show an improved pharmacokinetic profile over the immediate release Galantamine Hydrobromide 4 mg tablet (reference). Thereby, the inventive composition results in a decreased $c_{max}$ of Galantamine while maintaining an AUC of Galantamine ($AUC_{0-t}$ and $AUC_{0-\infty}$) comparable to the immediate release reference formulation (90% CI within 80-125% range for Galantamine) (Table 9).

A lower $C_{max}$ leads to a reduction of side effects associated with Galantamine, in particular gastrointestinal side effects, as side effects of a drug increase with the peak drug concentration present in blood/target organs. The observation of an equivalent AUC means that overall, the same amount of drug is being absorbed, (albeit at a slower rate), meaning that treatment effectiveness is maintained.

Due to the enteric coating of the inventive compositions the release of benzgalantamine occurs in the intestine above pH 5.5, resulting in a slower rise to $c_{max}$ of Galantamine ($T_{max}$ approx. 1.5 h for the inventive composition (test), from the time of first appearance of drug in plasma (Tlag)]) compared to the immediate release reference composition which results in the majority of Galantamine being absorbed in the stomach before reaching the intestine ($t_{max}$=1 h, with essentially no Tlag] (Table 7a). Both the rate at which plasma concentrations of benzgalantamine increase and the absolute concentration of benzgalantamine in plasma, influence the side effect profile. The slower rise to $c_{max}$ and lower $c_{max}$ of the inventive composition thus advantageously reduces gastrointestinal side effects.

The negligible (or below limit of quantitation) plasma benzgalantamine concentrations, observed after administration of the inventive composition further means that benzgalantamine is rapidly and completely or nearly completely converted to galantamine after release of the drug in the small intestine, advantageously resulting only in pharmacologically active galantamine and no or only negligible amounts of benzgalantamine being present in the systemic circulation of a subject.

After release of benzgalantamine from the inventive compositions in the intestine the drug is potentially subject to conversion to galantamine through esterase action in the following compartments: (a) in the lumen of the intestine [esterases resulting from microbial production], (b) during its transport across the intestinal wall (Ho et al. 2017, Xu et al. 2015), and (c) exposed to esterase activity in (portal) blood (Rudakova et al. 2010).

The results obtained within this study however show that even though benzgalantamine is converted to galantamine in any of the compartments (a), (b) and/or (c) the conversion surprisingly does not result in free galantamine concentrations in the gastrointestinal tract that are sufficiently high to provoke the side effect profile observed with the immediate release formulation. This represents a surprising effect, as it would have rather been expected that by conversion of benzgalantamine in compartments (a-c) after release in the intestine would have resulted in galantamine concentrations activating the enteric cholinergic nervous system, resulting in traditional gastrointestinal adverse events such as nausea, vomiting, diarrhea.

The inventive formulation comprising an enteric coating configured to release benzgalantamine at pH 5.5 or above thus surprisingly and advantageously provides protection against gastrointestinal adverse events, while achieving complete conversion of the prodrug to galantamine and a similar AUC compared to the immediate reference formulation.

Further, without being bound to theory, the results can be interpreted as that the rate ($T_{max}$ ca 1.5 h from $T_{lag}$) at which the drug is presented to the liver for first pass metabolism, is such that it doesn't overwhelm its metabolic capacity to completely/nearly completely, convert benzgalantamine to galantamine. This indicates in dose proportionality of the inventive composition and increases the safety profile and effectivity of the inventive compositions.

Example 3: Clinical Study (Benzgalantamine (ALPHA-1062) Delayed Release 5 mg Tablet Compared to ER Galantamine Hydrobromide 8 mg Tablet)

An open label, balanced, randomized, multiple dose, two-treatment, two arm, two-period, comparative steady state study of Benzgalantamine Delayed Release Tablets 5 mg (BID) in comparison with Razadyne® ER (galantamine extended-release capsules) 8 mg (QD) manufactured for Janssen Pharmaceuticals.

Test treatment (T): Benzgalantamine (ALPHA-1062) Delayed Release Tablets 5 mg according to the invention.

Reference treatment (R): Razadyne® ER (galantamine extended-release capsules) 8 mg.

Objectives and Endpoints:

Primary: Evaluation of the steady-state relative bioavailability (BA) of inventive benzgalantamine (ALPHA-1062) 5 mg delayed release tablets (BID, test) compared to 8 mg Razadyne® ER (galantamine extended-release capsules) (QD, reference) in healthy adult subjects.

Secondary: Evaluation of the safety and tolerability of administration of benzgalantamine delayed release tablets compared to Razadyne® ER (galantamine extended-release capsules) in healthy adult subjects.

Primary Endpoints: $AUC_{0-24}$, $C_{max,ss}$ (test and reference) on Day 7

Secondary Endpoints: Other parameters including but not limited to:

$C_{trough}$ Day 4 (equivalent to predose morning trough on Day 5)

$C_{trough}$ Day 5 (equivalent to predose morning trough on Day 6)

$C_{trough}$ Day 6 (equivalent to predose morning trough on Day 7)

$C_{trough}$ Day 7 (equivalent to 24 hour sample after Day 7 morning dose)

Day 7 pharmacokinetics: $AUC_{0-12,ss}$, $T_{max}$ (test and reference), $C_{max1}$ (test only), $C_{max2}$ (test only), $T_{max1}$ (test only), $T_{max2}$ (test only), $C_{avg}(AUC_{0-24}/24)$, $C_{min}$ (lowest concentration over 24 hours), $T_{min}$ (time of lowest concentration over 24 hours), $C_{trough}$ (concentration at the end of the dosing interval, i.e., $C_{24h}$—same as above), $C_{12h}$ (Test product trough for morning dose), CL/F (Apparent Clearance [Dose/$AUC_{0-24}$]), Flux (degree of fluctuation [$(C_{max}-C_{min})/C_{avg}$]), Swing [$(C_{max}-C_{min})/C_{min}$], $K_{el}$, $T_{1/2}$ Methodology:

Male and female study participants (in equal proportions) were enrolled in the study. A total of 52 normal, healthy, adult, human study participants were enrolled. All subjects either received test product or reference product in each period according to the randomization schedule after ensuring maintenance of pre-dose restrictions (fasting prior to administration in sitting posture with 240±2 mL of drinking water at ambient temperature).

A washout period of 6.5 days was observed between both the study periods. Study restrictions with respect to fluid intake and sitting positions were implemented during the restriction periods throughout the study in all periods. The total duration of participation for each subject was approximately 51 days including screening.

In each period, on Dosing days (1-7), subjects received either twice daily dosing of 5 mg benzgalantamine delayed release tablet (test) or once daily dosing of 8 mg RAZADYNE® ER (galantamine hydrobromide) extended-release capsule (reference) in a crossover fashion, as per randomization scheme.

Study participants were instructed not to break, cut and chew the tablets or capsules, but to swallow whole and were asked to take it with specified quantity of water. Water intake was not allowed for 1 hour before dosing until 1 hour after dosing except while administration of the dose. After dosing, the participants remained in seated for the first 2 hours post dose. On dosing days, meals were given as per the following schedule. Meals were the same for all study participants in all the periods.

TABLE 11

Schedule of standardized meals

| Day | Breakfast | Lunch | Snacks | Dinner |
|---|---|---|---|---|
| D-1 | — | — | — | 11 hours pre-dose |
| Dosing day (D) - Day 1 | 1 hours post morning dose | 5 hours post morning dose | 9 hours post morning dose | 13 hours post morning dose |
| Dosing day (D) - Day 2 | 1 hours post morning dose | 5 hours post morning dose | 9 hours post morning dose | 13 hours post morning dose |
| Dosing day (D) - Day 3 | 1 hours post morning dose | 5 hours post morning dose | 9 hours post morning dose | 13 hours post morning dose |
| Dosing day (D) - Day 4 | 1 hours post morning dose | 5 hours post morning dose | 9 hours post morning dose | 13 hours post morning dose |
| Dosing day (D) - Day 5 | 2 hours post morning dose | 6 hours post morning dose | 9.5 hours post morning dose | 14 hours post morning dose |
| Dosing day (D) - Day 6 | 2 hours post morning dose | 6 hours post morning dose | 9.5 hours post morning dose | 13 hours post morning dose |
| Dosing day (D) - Day 7 | — | 5 hours post morning dose | 9.5 hours post morning dose | 14 hours post morning dose |
| Day - 8 | 24 hours post morning dose of Day 7 | 28 hours post morning dose of Day 7 | 32 hours post morning dose of Day 7 | 36 hours post morning dose of Day 7 |
| Day - 9 | 48 hours post morning dose of Day 7 | 52 hours post morning dose of Day 7 | 56 hours post morning dose of Day 7 | — |

Post dose meals were uniform in all the clinical periods and served at the same time in each study period.

Study participants were served dinner to maintain following criteria:

In each period, Dosing occurs on Days 1-7 inclusive.

Days 5 & 6 Morning dosing: Pre-dose on mornings of Days 5 and 6, subjects were fasted for at least 8 hours, have their pharmacokinetic (PK) sample for $C_{trough}$ taken before dosing, and then fast for 2 hours post-morning dose on Days 5 and 6.

Day 7 Morning dosing: Beginning on the evening of Day 6, subjects fasted for at least 10 hours before morning dosing on Day 7, have their PK sample for $C_{trough}$ taken before dosing, and then fasted for at least 5 hours after the morning dosing on Day 7.

Day 5 and 7 Evening Dosing: Subjects fasted for at least 2 hours before and 2 hours after evening dose.

Day 6 Evening Dosing: Subjects fasted for at least 2 hours before and 1 hour after evening dose.

Day 1-4: Study participants fasted for at least 10 hours prior to the morning drug administration.

Evening dose of test product was administered at 12 hours post morning dose.

When confined, standard meals and snacks were provided at appropriate times, except when they are required to fast. Study participants fasted for at least 10 hours prior to morning drug administration on Day 1 to Day 4. When confined in the Clinical Pharmacology Unit (CPU), study participants fasted from all food and drink except water between meals and snacks.

Study Participants:

52 study participants were enrolled, among them 47 participants were found eligible for the study. Signed informed consent form was obtained from each volunteer before enrolling them in the study. Healthy adult human male and female participants between 18-70 years of age with a body mass index between ≥18.0 kg/m² and ≤30.0 kg/m² at the screening visit were enrolled. 40 study participants completed all the study periods and were included for pharmacokinetic analysis and 38 study participants were included for Statistical analysis.

Further Study Activities:

Presentation and obtaining of informed consent form, urine drug screening including alcohol, vitals, physical examination, C-SSRS assessment, serum pregnancy test (only for female study participants), Covid Rapid Antigen test, 12-Lead ECG, body and baggage search, maintenance of pre-dose restrictions and provision of uniform diet on check in day. A blood sample for evaluation of CYP2D6 Genotype was collected during Period-I check-in only. Body weight (kg) was recorded at the time of check-in and check-out of each period. ECG was measured at the time of check-in, 3 hours post morning dose (±60 minutes) of Day 7 in each period and at the time of checkout commencing from 180 minutes prior to checkout in each period. Pre-dose safety monitoring, dosing, sample collection and processing as well as safety monitoring, maintenance of post-dose restrictions and uniform diet was provided throughout their stay.

TABLE 12

Investigational Products, Dose, Mode of Administration and Lot/Batch Number.

| Test Product: T (test) | Reference Product: R (reference) |
|---|---|
| Benzgalantamine (gluconate form A) delayed-release tablet 5 mg | Razadyne ® ER (galantamine extended-release capsules) 8 mg Each capsule Contains 8 mg of galantamine as 10.25 mg galantamine hydrobromide |
| Manufactured for: Alpha Cognition, Inc. | Manufactured for: Janssen Pharmaceuticals, Inc., Titusville, NJ 08560 |
| Dose and Mode of Administration: Single dose for (morning & evening) multiple days, oral. | Dose and Mode of Administration: Single dose for (morning) multiple days, oral. |
| Storage conditions: 20° C.-25° C.; Excursions permitted to 15° C.-30° C. | Storage conditions: 25° C.; excursions permitted between 15° C. to 30° C. |

Pharmacokinetic Blood Sampling:

A total of 38 blood sampling time points were collected for test treatment including Pre-dose (0 hour) and post-dose samples in each period for measuring Galantamine and benzgalantamine. A total of 25 blood sampling time points were collected for reference treatment including Pre-dose (0 hour) and post-dose samples in each period for measuring Galantamine. In each period, 2 samples of pre-dose i.e., 0 hours pre-dose (each 5 mL) on Day1 was collected within 1 hour prior to drug administration. Pre-dose samples i.e., 0 hours pre-dose (each 5 mL) on Day 5, 6 and 7 were collected within 0-10 minutes prior to dosing. Morning pre-dose samples were collected on Days 5, 6 and 7 for $C_{trough}$ for both reference and test.

On Day 7 for test—Post morning dose samples were collected at 0.25, 0.5, 0.75, 1, 1.5, 2, 2.5, 3, 3, 4, 4.5, 5, 6, 8, 12, 12.25, 12.5, 12.75, 13, 13.5, 14, 14.5, 15, 15.5, 16, 16.5, 17, 18, 20, 24, 28, 36, 48 and 60 hours. On Day 7 for reference—Post morning dose samples were collected at 0.50, 1, 1.5, 2, 2.5, 3, 3.5, 4, 4.5, 5, 5.5, 6, 6.5, 7, 8, 12, 16, 24, 36, 48 and 60 hours.

The total volume of blood collected per study participant in this study was not exceed 384 mL for male and 388 mL for female including 9 mL for screening, 7-9 mL for post clinical assessment of lab parameters, and 26 mL for discarding saline mixed blood sample resulting from use of intravenous cannula for 24 hours on day 7 and an additional 2-9 mL which may be collected for repeat/additional lab tests, if required. Blood samples were collected by direct venipuncture on Day 1, 5 & 6 and by means of intravenous cannula until 24 hours post morning dose of Day 7 using pre-labelled 5 mL K₂EDTA vacutainers.

After collection, the blood samples were placed in wet ice bath condition to maintain the temperature at below 15° C. Once blood samples from all the study participants at each time point were available, they were centrifuged at 3800 rpm for 10 minutes at 10° C.±2° C. for separating the plasma. Centrifugation of all samples were done within 45 minutes after each sample draw time point. All plasma samples were separated and divided into two aliquots i.e. at least 1 mL in aliquot #1 and remaining plasma in aliquot #2 in properly labelled polypropylene tubes and immediately stored at −20° C.±4° C. until completion of analysis. After the analysis the plasma samples were retained for a duration of 90 days from the date of report submission to the sponsor or as per the sponsor requirement. The time from sample collection to placement in the freezer did not exceed 120 minutes. Plasma samples were analyzed for benzgalantamine (ALPHA-1062) and Galantamine using LC-MS/MS analysis. All the clinical activities were performed under yellow monochromatic light conditions.

Pharmacokinetic Analysis:

The following pharmacokinetic parameters were calculated for benzgalantamine and Galantamine in plasma using Phoenix® WinNonlin® 8.0 or higher version (Pharsight Corporation, USA) or SAS® 9.4 with Enterprise Guide 7.1 or higher version.

Primary parameters: $AUC_{0-24,ss}$ and $C_{max,ss}$

| | |
|---|---|
| $AUC_{0-24,ss}$ | The daily area under the concentration-time curve at steady state, as calculated by the linear trapezoidal method. |
| $C_{maxss}$ | Maximum observed concentration at steady state. |

Secondary parameters: $C_{trough}$ Day 4, $C_{trough}$ Day 5, $C_{trough}$ Day 6, $C_{trough}$ Day 7, $C_{12h}$, $AUC_{0-12,ss}$, $T_{max,ss}$, $C_{max1,ss}$, $C_{max2,ss}$, $T_{max1,ss}$, $T_{max2,ss}$, $C_{avg}(AUC_{0-24/24})$, $C_{min}$ (lowest concentration over 24 hours), $T_{min}$ (Time of lowest concentration over 24 hours), $K_{el}$, $t_{1/2}$, CL/F (Apparent Clearance [Dose/$AUC_{0-24}$]), % FLUX (degree of fluctuation [$(C_{max}-C_{min})/C_{avg}$]), Swing [$(C_{max}-C_{min})/C_{min}$].

| | |
|---|---|
| $C_{trough}$ Day 4 | Concentration observed at the end of the Day 4 dosing interval (equivalent to predose morning trough on Day 5). |
| $C_{trough}$ Day 5 | Concentration observed at the end of the Day 5 dosing interval (equivalent to predose morning trough on Day 6). |
| $C_{trough}$ Day 6 | Concentration observed at the end of the Day 6 dosing interval (equivalent to predose morning trough on Day 7). |
| $C_{trough}$ Day 7 | Concentration observed at the end of the Day 7 dosing interval (equivalent to 24 hours sample after Day 7 morning dose [$C_{24h}$]). |
| $C_{12h}$ | Concentration observed at 12 hours post Day 7 morning dose. |
| $AUC_{0-12,ss}$ | The area under the concentration-time curve from time '0' to 12 hours post dose at steady state, as calculated by the linear trapezoidal method. |
| $T_{max,ss}$ | Time to reach $C_{max}$. If the maximum value occurs at more than one time point within the dosing interval(s), $T_{max,ss}$ is defined as the first time point with this value. |
| $C_{max1,ss}$ | Maximum observed concentration during morning dosing interval at steady state (Test product only). |
| $C_{max2,ss}$ | Maximum observed concentration during evening dosing interval at steady state (Test product only). |
| $T_{max1,ss}$ | Time to reach $C_{max1,ss}$. If the maximum value occurs at more than one time point within the dosing interval, $T_{max1,ss}$ is defined as the first time point with this value (Test product only). |
| $T_{max2,ss}$ | Time to reach $C_{max2,ss}$. If the maximum value occurs at more than one time point within the dosing interval, $T_{max2,ss}$ is defined as the first time point with this value (Test product only). |
| $C_{avg,ss}$ | Average daily concentration over the dosing interval(s) at steady state, calculated as $AUC_{0-24/24}$ |
| $C_{min,ss}$ | Minimum observed concentration over 24 hours at steady state. |
| $T_{min,ss}$ | Time of minimum observed concentration over 24 hours at steady state. |
| $K_{el}$ | Apparent first-order terminal elimination rate constant calculated from a semi-log plot of the plasma concentration versus time curve. The parameter was calculated by linear least-squares regression analysis using the maximum number of points in the terminal log-linear phase (e.g., three or more non-zero plasma concentrations). |
| $t_{1/2}$ | Apparent first-order terminal elimination half-life was calculated as 0.693/Kel. |
| $CL_{ss/F}$ | Apparent total plasma clearance after oral (extravascular) administration, calculated as Dose/$AUC_{0-24,ss}$. |
| % FLUX | Degree of peak-to-trough fluctuation expressed as a percentage, calculated as follows: ($[C_{max,ss} - C_{min,ss}]/C_{avg,ss}$) * 100. |
| Swing | Swing, calculated as follows: ($[C_{max,ss} - C_{min,ss}]/C_{min,ss}$). |

Gastrointestinal Adverse Events:

The safety assessments performed during the study included but not limited to body weight assessment, blood samples for organ function, adverse event monitoring, vital sign monitoring, and cardiology and physical assessments. Adverse event (AE) monitoring was done throughout the course of the study by clinical examination, vitals check, and participant observation of well-being.

Statistical Analysis & Descriptive Statistics:

Statistical analysis was performed on pharmacokinetic data of samples assayed and quantified for Galantamine in plasma. The ln-transformed pharmacokinetic parameters $AUC_{0-24}$ and $C_{max}$ for Galantamine will be statistically analyzed using linear mixed effects model using the SAS® system version 9.4 or higher with Enterprise Guide 7.1 or higher version for Windows, (SAS® Institute Inc. USA). The descriptive statistics (such as count (N), mean, median, minimum, maximum, standard deviation (SD) and coefficient of variation (CV) for the relevant pharmacokinetic parameters were estimated for both the Tests and Reference formulations. The geometric mean and coefficient of variation were estimated for $AUC_{0-24}$, $C_{max}$, $AUC_{0-12}$, $T_{max}$, $C_{max1}$ (test only), $C_{max2}$ (test only), $T_{max1}$ (test only), $T_{max2}$ (test only), $C_{avg}$ ($AUC_{0-24/24}$), $C_{min}$ (lowest concentration over 24 hours), $T_{min}$ (Time of lowest concentration over 24 hours), $C_{trough}$ (concentration at the end of the dosing interval, i.e., $C_{24h}$), $C_{12h}$ (test product trough for morning dose), CL/F (Apparent Clearance [Dose/$AUC_{0-24}$]), Flux (degree of fluctuation [$(C_{max}-C_{min})/C_{avg}$]), Swing [$(C_{max}-C_{min})/C_{min}$], $K_{el}$ und $T_{1/2}$. In this study, inferential statistics linear regression model was used.

Assessment of Bioavailability:

Similarity in bioavailability was concluded if the 90% confidence intervals for the ratios of least squares means of the PK parameters $AUC_{0-24,ss}$ and $C_{max,ss}$ for galantamine fall within the reference range of 80 and 125%. In addition, the peak exposure of the test product ($C_{max,ss}$) would be concluded to be not inferior to that of the reference product if the entire 90% Cl for the ratio of least square mean of the PK parameter $C_{max,ss}$ for galantamine falls above the 80% lower reference limit.

Determination of Sample Size

A total of 40 normal healthy adult, male and female study participants were dosed in the study.

T/R ratio=90%-111%

Expected Intra-Subject C.V (%)~18%

Significance Level=5%

Power=80%

Bioequivalence Limits=80-125%

Based on the above estimate, calculated sample size of 40 study participants were sufficient to establish bioequivalence between two formulations with adequate power, considering 10% dropouts due to adverse events or non-compliance or due to personal reasons. 40 healthy adult, male and female study participants were sufficient for the study.

Results

Demographics and Other Baseline Characteristics

TABLE 13

Demographics summary of all participants within the study (N = 38).

| Parameters | Age (yrs) | Weight (kg) | Height (cms) | BMI (kg/m²) |
|---|---|---|---|---|
| Mean (SD) | 35.9 (9.06) | 66.1 (9.68) | 160.1 (9.20) | 25.7 (2.49) |
| Median | 35.5 | 64.0 | 158.8 | 25.7 |
| CV % | 25.2 | 14.7 | 5.7 | 9.7 |
| Range | 21.0-56.0 | 50.0-90.9 | 143.5-179.0 | 20.0-29.9 |

Treatment Compliance

All the study participants ingested the study drug; this was confirmed by direct observation of administration of study drug as well as by performing hand and mouth checks and further ascertained by the presence of plasma benzgalantamine and Galantamine concentrations in individual blood samples following drug administration.

Pharmacokinetic Results:

The pharmacokinetic parameters were calculated by linear mixed effects model. The pharmacokinetic parameters were statistically analyzed to compare the Test and Reference formulations in regard to $C_{max,ss}$, and $AUC_{0-24}$.

Figure 4:
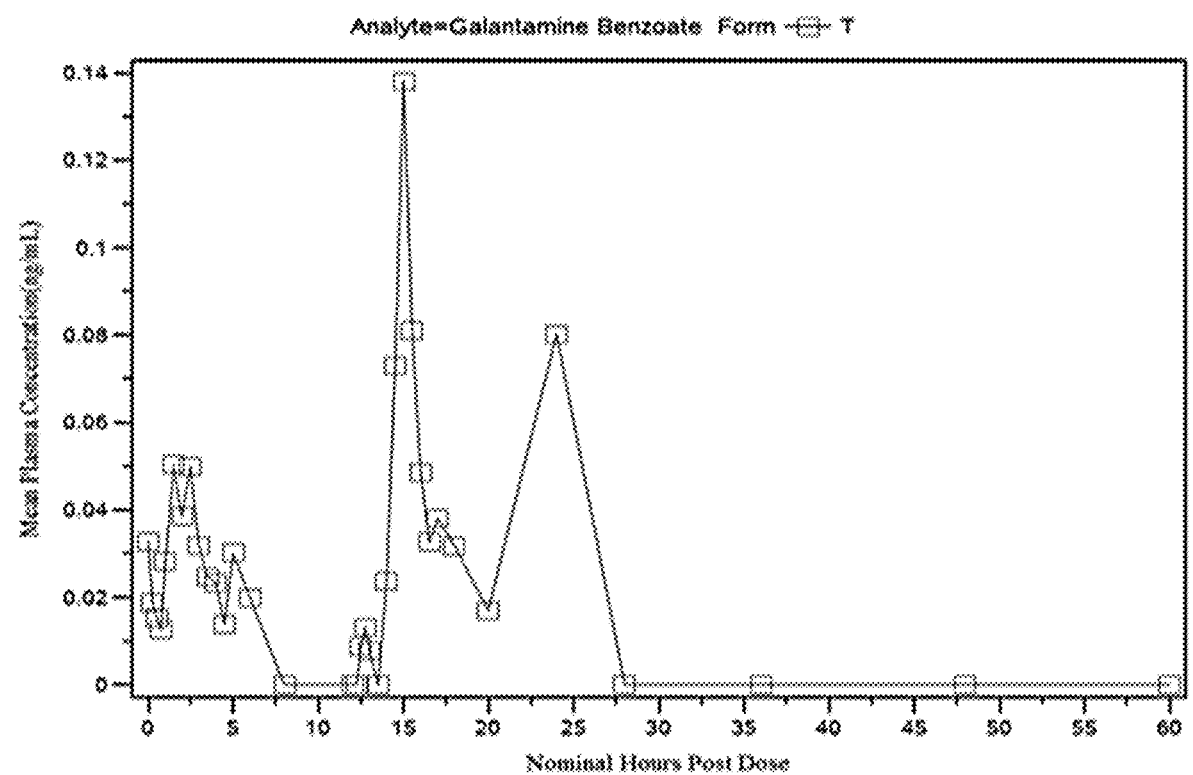
FIG. 4: Mean plasma benzgalantamine concentrations Vs. Time Plots-Linear Scale. Clinical study evaluating inventive benzgalantamine delayed-release tablets, 5 mg vs. Razadyne® ER (galantamine extended-release capsules) 8 mg.
Figure 5:
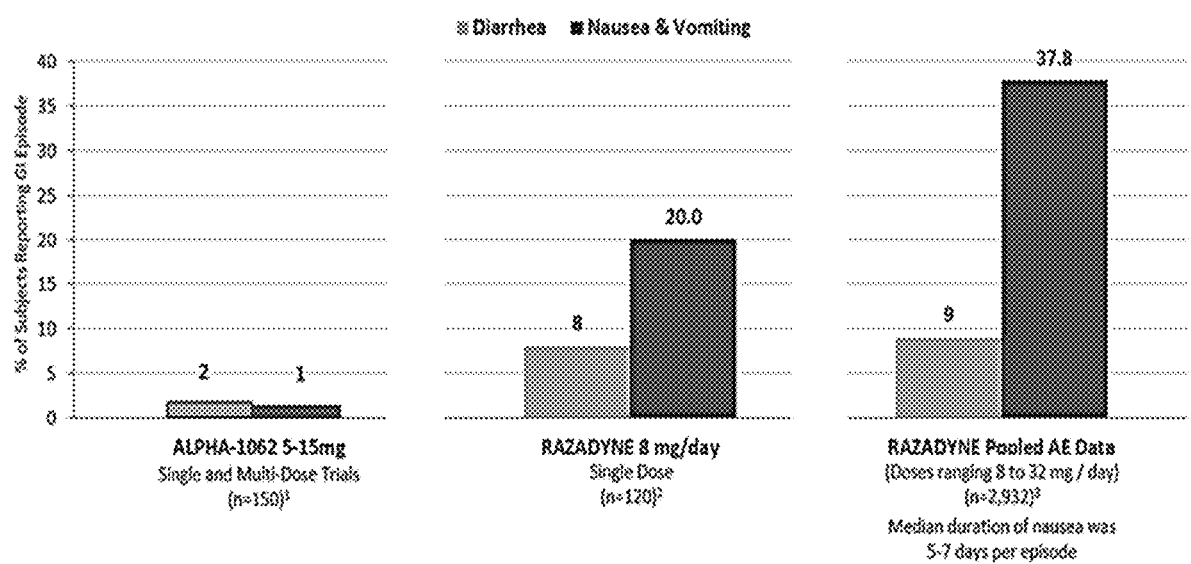
FIG. 5: Comparison of the incidence of gastrointestinal adverse events in subjects who were treated with the inventive pharmaceutical composition comprising benzgalantamine or a single dose galantamine composition (Razadyne® ER (galantamine extended-release capsules) 8 mg). [1]The benzgalantamine data was consolidated from different clinical studies, including the bioequivalence trial of benzgalantamine vs IR (Example 2: benzgalantamine Delayed Release Tablet 5 mg tablet (T) vs. Galantamine Hydrobromide (Yabao) 4 mg tablet (RT)) and the bioequivalence trial of benzgalantamine vs. ER (Example 3: benzgalantamine (delayed-release tablets 5 mg vs. Razadyne® ER (galantamine extended-release capsules) 8 mg). [2] ISSD: completed Phase 1 trials in healthy adults; J&J Reminyl NDA package submission (prior art). [3] RAZADYNE full prescribing information (prior art).

The mean plasma concentration versus scheduled time plots (linear and log-linear scales) for Galantamine were obtained and are presented in FIG. 3. The mean plasma concentration versus scheduled time plots (linear and log-linear scales) for benzgalantamine were obtained and are presented in FIG. 4.

TABLE 14

Arithmetic Mean (SD) of Pharmacokinetic Parameters of Galantamine.

| | Galantamine | | | |
|---|---|---|---|---|
| PK Parameter (Units) | N | Treatment T (Test) | N | Treatment R (Reference) |
| $C_{maxss}$ | 40 | 42.101 (8.602) | 40 | 33.435 (6.825) |
| $AUC_{0\_24ss}$ | 40 | 533.947 (113.993) | 40 | 501.154 (122.33) |
| $AUC_{0\_12ss}$ | 40 | 280.211 (54.375) | 40 | 312.845 (69.029) |
| Fluctuation % | 40 | 134.479 (34.811) | 40 | 106.521 (25.862) |
| $C_{avg}$ | 40 | 22.876 (4.478) | 40 | 23.416 (5.677) |
| $C_{tau}$ | 40 | 16.283 (4.548) | 40 | 16.293 (7.073) |
| $C_{minss}$ | 40 | 11.897 (3.564) | 40 | 9.333 (3.53) |
| CLss_F | 40 | 0.017 (0.004) | 40 | 0.017 (0.004) |
| Swing | 40 | 2.844 (1.393) | 40 | 2.898 (1.131) |
| $T_{maxss}$ | 40 | 3 (1, 15.5) | 40 | 5 (1, 6.5) |
| HL_Lambda_z | 40 | 11.533 (1.471) | 40 | 12.69 (1.977) |
| Lambda_z | 40 | 0.061 (0.008) | 40 | 0.056 (0.009) |
| $T_{minss}$ | 40 | 6.885 (6.492) | 40 | 3.038 (8.025) |

*For $T_{max,SS}$, Median (Min, Max) are presented.

TABLE 15

Statistical Results of Assessment of bioavailability of
Galantamine steady state study benzgalantamine
Delayed Release Tablets 5 mg (Form T) with Razadyne ® ER
(Galantamine extended-release capsules) 8 mg (Form R).

| PK Parameter | Geometric Means | | Ratio | CV % | 90% Confidence Interval | Power: |
|---|---|---|---|---|---|---|
| | Test | Reference | | | | |
| Ln-transformed: | | | | | | |
| Log ($C_{maxss}$) (ng/ml) | 41.6814 | 32.8507 | 126.88 | 13.12 | (120.62, 133.47) | 1.62 |
| log($AUC_{[0-24]ss}$) (ng · hr/mL) | 527.4567 | 492.0781 | 107.19 | 8.41 | (103.76, 110.73) | 100.00 |

TABLE 16

Analysis of Variance for Galantamine
(test (T) Vs reference (R))

| PK Parameter | P-Value | | |
|---|---|---|---|
| | Sequence | Period | Treatment |
| Log ($C_{maxss}$)(ng /mL) | 0.3199 | 0.0164* | 0.0000* |
| log($AUC_{[0-4]ss}$)(ng · hr/mL) | 0.7814 | 0.0020* | 0.0009* |

The GM Ratio with 90% CI of Ratio galantamine estimates of $C_{max,ss}$ and $AUC_{0-24ss}$ values of the benzgalantamine delayed release tablet 5 mg (Test) over those of the Razadyne® ER (galantamine extended-release capsules) 8 mg (reference) were 126.88 (120.62, 133.47) and 107.19 (103.76, 110.73) respectively (Table 15). The 90% CI for $AUC_{0-24,ss}$ of the inventive composition (test) was within 80-125% range for Galantamine (Table 15). The two formulations i.e., benzgalantamine delayed release Tablet 5 mg (test) and Razadyne® ER (galantamine extended-release capsules) 8 mg (reference) are similar in bioavailability under fasting condition.

Gastrointestinal Adverse Events

TABLE 17

Incidence of gastrointestinal adverse events.

| Body System/ Adverse Event | Reported Incidence by Treatment Groups Fasting Bioequivalence Study Study No. 03333/22-23 | |
|---|---|---|
| | Test Treatment (T) | Reference Treatment (R) |
| Gastro Intestinal Disorders | | |
| Nausea | — | 1 (2.5%) |
| Vomiting | — | 1 (2.5%) |
| Diarrhea | 1 (2.5%) | — |
| Total | 1 (2.5 %) | 2 (5%) |

N = Number of subjects with incidence of adverse events (AEs).
% = Percentage of the adverse event calculated by total number of study subjects that participated in the study A total of 3 gastrointestinal adverse events (AE) were reported. Of these 3 AE, 2 AE (i.e., Nausea and Vomiting) were reported during period-I, 1 AE (i.e., Diarrhea) was reported during period-II. No Serious Adverse Events, Significant Adverse Events or Deaths occurred in this study.

Overall subjects who were administered the inventive compositions showed lower incidence of gastrointestinal adverse events in comparison to the RAZADYNE® galantamine extended-release capsules 8 mg (reference) (Table 17). This further demonstrates that the inventive composition comprising benzgalantamine and an enteric coating configured for dissolution at pH 5.5 or above shows an advantageous dissolution and release profile and improved pharmacokinetic properties in comparison to the reference composition comprising Galantamine, advantageously resulting in a reduced incidence of gastrointestinal adverse events.

CONCLUSION

Overall, the inventive compositions show an improved pharmacokinetic profile over the Razadyne® ER (galantamine extended-release capsules) 8 mg (reference). Thereby, the inventive composition results in an increased $c_{max,ss}$ of Galantamine while maintaining an AUC of Galantamine ($AUC_{0-24,ss}$) comparable to the extended release reference formulation (90% CI within 80-125% range for Galantamine) (Table 14 and 15).

A higher $C_{max}$ leads to high levels of efficacy, while the observation of an equivalent AUC means that overall, the same amount of drug is being absorbed.

A higher $C_{max,ss}$ of Galantamine for the inventive compositions compared to Razadyne® ER (galantamine extended-release capsules) 8 mg (reference) but the same AUC result in greater benefit to the patient and is desirable. Whereas the comparative Razadyne® ER (galantamine extended-release capsules) 8 mg (reference) provides constant slow release of galantamine the inventive compositions provide a more acute release of benzgalantamine followed by conversion to galantamine after the pH sensitive enteric coat breaks in the intestine at pH 5.5 or above.

The inventive compositions resulting in a higher $c_{max}$ than the Razadyne® ER (galantamine extended-release capsules) 8 mg (reference), but a lower $c_{max}$ than the immediate release galantamine 4 mg tablets (reference example 3) and a similar AUC to both reference formulations thus provide a benefit to a patient over both reference formulations, as adverse effects, in particular gastrointestinal adverse events are reduced while treatment efficacy is maintained. Such beneficial effect of the inventive compositions could not have been expected by person skilled in the art.

Example 4: Alcohol Dose Dumping Study of Inventive Benzgalantamine Tablets

The purpose of this study was to evaluate the effect of alcohol on the release rate of benzgalantamine (ALPHA-1062) from inventive benzgalantamine delayed release tablets (5 mg and 15 mg).

Experimental Approach

Dissolution testing (n=12) was performed according to TP81939 for one lot of each strength of Galantamine benzoate delayed release tablets (5 mg and 15 mg) using each of the dissolution media described in the method (0%, 5% and 20% ethyl alcohol) benzgalantamine (ALPHA-1062) Delayed Release tablets are tested by two stage dissolution, first in acidic stage followed by buffer stage. The dissolution is conducted as per the USP <711> method using Apparatus I at temperature of 37.0±0.5° C., with basket rotation of 50 RPM. The dissolution media is 5% and 20% ethyl alcohol in 1000 ml of 0.01 N Hydrochloric acid or phosphate buffer pH 6.8. The duration of dissolution testing is 2 hours in acid stage and 75 minutes in buffer stage. Percent dissolved results were calculated according to the method.

Results

TABLE 18a

0% Ethyl Alcohol Medium Results - Acid Stage
(benzgalantamine (ALPHA-1062) delayed release tablets 5 mg)

| | % Dissolved | | | |
|---|---|---|---|---|
| Vessel | 30 Minutes | 60 Minutes | 90 Minutes | 120 Minutes |
| 1 | ND | ND | ND | ND |
| 2 | ND | ND | ND | ND |
| 3 | ND | ND | ND | ND |
| 4 | ND | ND | ND | ND |
| 5 | ND | ND | ND | ND |
| 6 | ND | ND | ND | ND |
| 7 | ND | ND | ND | ND |
| 8 | ND | ND | ND | ND |
| 9 | ND | ND | ND | ND |
| 10 | ND | ND | ND | ND |
| 11 | ND | ND | ND | ND |
| 12 | ND | ND | ND | ND |
| Mean | — | — | — | — |
| % RSD | — | — | — | — |

TABLE 18b

0% Ethyl Alcohol Medium Results - Buffer Stage
(benzgalantamine (ALPHA-1062) delayed release tablets 5 mg)

| | % Dissolved | | | | | | |
|---|---|---|---|---|---|---|---|
| Vessel | 15 Minutes | 20 Minutes | 25 Minutes | 30 Minutes | 45 Minutes | 60 Minutes | Infinity (+15 Minutes at 250 RPM) |
| 1 | 39 | 60 | 76 | 90 | 98 | 97 | 96 |
| 2 | 21 | 34 | 51 | 73 | 94 | 96 | 97 |
| 3 | 24 | 39 | 59 | 77 | 97 | 99 | 99 |
| 1 | 17 | 38 | 56 | 82 | 94 | 98 | 96 |
| 5 | 14 | 29 | 53 | 70 | 93 | 95 | 95 |
| 6 | 16 | 35 | 59 | 78 | 96 | 99 | 100 |
| 7 | 32 | 45 | 66 | 82 | 97 | 98 | 99 |
| 8 | 28 | 50 | 61 | 82 | 96 | 96 | 95 |
| 9 | 26 | 50 | 63 | 75 | 94 | 93 | 91 |
| 10 | 30 | 48 | 64 | 81 | 93 | 96 | 91 |
| 11 | 21 | 39 | 55 | 70 | 94 | 98 | 97 |
| 12 | 28 | 44 | 62 | 77 | 96 | 94 | 96 |
| Mean | 25 | 43 | 60 | 78 | 95 | 97 | 96 |
| % RSD | 29.6 | 20.2 | 11.1 | 7.4 | 1.8 | 2.0 | 2.9 |

TABLE 19a

5% Ethyl Alcohol Medium Results - Acid Stage
(benzgalantamine (ALPHA-1062) delayed release tablets 5 mg)

| | % Dissolved | | | |
|---|---|---|---|---|
| Vessel | 30 Minutes | 60 Minutes | 90 Minutes | 120 Minutes |
| 1 | ND | ND | ND | ND |
| 2 | ND | ND | ND | ND |
| 3 | ND | ND | ND | ND |
| 4 | ND | ND | ND | ND |
| 5 | ND | ND | ND | ND |
| 6 | ND | ND | ND | ND |
| 7 | ND | ND | ND | ND |
| 8 | ND | ND | ND | ND |
| 9 | ND | ND | ND | ND |
| 10 | ND | ND | ND | ND |
| 11 | ND | ND | ND | ND |
| 12 | ND | ND | ND | ND |
| Mean | — | — | — | — |
| % RSD | — | — | — | — |

TABLE 19b

5% Ethyl Alcohol Medium Results - Buffer Stage (benzgalantamine (ALPHA-1062) delayed release tablets 5 mg)

| | % Dissolved | | | | | | |
|---|---|---|---|---|---|---|---|
| Vessel | 15 Minutes | 20 Minutes | 25 Minutes | 30 Minutes | 45 Minutes | 60 Minutes | Infinity (+15 Minutes at 250 RPM) |
| 1 | 12 | 32 | 49 | 60 | 92 | 100 | 103 |
| 2 | 17 | 43 | 56 | 67 | 92 | 94 | 96 |
| 3 | 11 | 36 | 53 | 67 | 90 | 91 | 91 |
| 4 | 11 | 34 | 51 | 64 | 91 | 93 | 92 |
| 5 | 43 | 61 | 75 | 86 | 96 | 96 | 97 |
| 6 | 16 | 43 | 56 | 70 | 97 | 99 | 97 |
| 7 | 15 | 43 | 57 | 74 | 98 | 102 | 101 |
| 8 | 32 | 55 | 70 | 81 | 100 | 103 | 102 |
| 9 | 31 | 51 | 61 | 75 | 92 | 96 | 96 |
| 10 | 11 | 39 | 55 | 73 | 92 | 93 | 94 |

TABLE 19b-continued

5% Ethyl Alcohol Medium Results - Buffer Stage
(benzgalantamine (ALPHA-1062) delayed release tablets 5 mg)

% Dissolved

| Vessel | 15 Minutes | 20 Minutes | 25 Minutes | 30 Minutes | 45 Minutes | 60 Minutes | Infinity (+15 Minutes at 250 RPM) |
|---|---|---|---|---|---|---|---|
| 11 | 39 | 55 | 68 | 80 | 95 | 95 | 95 |
| 12 | 17 | 40 | 56 | 70 | 92 | 95 | 95 |
| Mean | 21 | 44 | 59 | 72 | 94 | 96 | 97 |
| % RSD | 55.0 | 20.7 | 13.6 | 10.4 | 3.4 | 3.9 | 3.9 |

TABLE 20a

20% Ethyl Alcohol Medium Results - Acid Stage
(benzgalantamine (ALPHA-1062) delayed release tablets 5 mg)

% Dissolved

| Vessel | 30 Minutes | 60 Minutes | 90 Minutes | 120 Minutes |
|---|---|---|---|---|
| 1 | ND | ND | ND | ND |
| 2 | ND | ND | ND | ND |
| 3 | ND | ND | ND | ND |
| 4 | ND | ND | ND | ND |
| 5 | ND | ND | ND | ND |
| 6 | ND | ND | ND | ND |
| 7 | ND | ND | ND | ND |
| 8 | ND | ND | ND | ND |
| 9 | ND | ND | ND | ND |
| 10 | ND | ND | ND | ND |
| 11 | ND | ND | 4 | 13 |
| 12 | ND | ND | ND | ND |
| Mean | — | — | — | — |
| % RSD | — | — | — | — |

TABLE 20b

20% Ethyl Alcohol Medium Results - Buffer Stage
(benzgalantamine (ALPHA-1062) delayed release tablets 5 mg)

% Dissolved

| Vessel | 15 Minutes | 20 Minutes | 25 Minutes | 30 Minutes | 45 Minutes | 60 Minutes | Infinity (+15 Minutes at 250 RPM) |
|---|---|---|---|---|---|---|---|
| 1 | 72 | 92 | 97 | 98 | 98 | 98 | 98 |
| 2 | 53 | 82 | 93 | 96 | 96 | 95 | 97 |
| 3 | 52 | 79 | 91 | 95 | 95 | 96 | 95 |
| 4 | 46 | 83 | 94 | 94 | 95 | 96 | 95 |
| 5 | 47 | 83 | 94 | 96 | 95 | 96 | 95 |
| 6 | 72 | 91 | 94 | 97 | 95 | 95 | 96 |
| 7 | 75 | 92 | 94 | 94 | 94 | 94 | 99 |
| 8 | 54 | 75 | 88 | 89 | 89 | 89 | 89 |
| 9 | 60 | 81 | 90 | 90 | 90 | 90 | 90 |
| 10 | 47 | 81 | 88 | 91 | 91 | 91 | 91 |
| 11 | 56 | 74 | 77 | 77 | 77 | 771 | 77 |
| 12 | 35 | 77 | 89 | 94 | 95 | 95 | 95 |
| Mean | 56 | 83 | 91 | 93 | 93 | 93 | 93 |
| % RSD | 21.8 | 7.6 | 5.7 | 6.1 | 6.0 | 6.1 | 6.4 |

TABLE 21a

0% Ethyl Alcohol Medium Results - Acid Stage
(benzgalantamine (ALPJHA-1062) delayed release tablets 15 mg)

| | % Dissolved | | | |
|---|---|---|---|---|
| Vessel | 30 Minutes | 60 Minutes | 90 Minutes | 120 Minutes |
| 1 | ND | ND | ND | ND |
| 2 | ND | ND | ND | ND |
| 3 | ND | ND | ND | ND |
| 4 | ND | ND | ND | ND |
| 5 | ND | ND | ND | ND |
| 6 | ND | ND | ND | ND |
| 7 | ND | ND | ND | ND |
| 8 | ND | ND | ND | ND |
| 9 | ND | ND | ND | ND |
| 10 | ND | ND | ND | ND |
| 11 | ND | ND | ND | ND |
| 12 | ND | ND | ND | ND |
| Mean | — | — | — | — |
| % RSD | — | — | — | — |

TABLE 21b

0% Ethyl Alcohol Medium Results - Buffer Stage
(benzgalantamine (APLHA-1062) delayed release tablets 15 mg)

| | % Dissolved | | | | | | |
|---|---|---|---|---|---|---|---|
| Vessel | 15 Minutes | 20 Minutes | 25 Minutes | 30 Minutes | 45 Minutes | 60 Minutes | Infinity (+15 Minutes at 250 RPM) |
| 1 | 15 | 37 | 53 | 67 | 89 | 97 | 100 |
| 2 | 11 | 26 | 37 | 49 | 80 | 96 | 99 |
| 3 | 12 | 22 | 30 | 46 | 84 | 106 | 110 |
| 4 | 16 | 27 | 38 | 54 | 87 | 99 | 100 |
| 5 | 19 | 27 | 41 | 58 | 90 | 103 | 104 |
| 6 | 15 | 31 | 44 | 57 | 83 | 98 | 102 |
| 7 | 17 | 24 | 36 | 51 | 87 | 98 | 99 |
| 8 | 12 | 21 | 41 | 52 | 81 | 91 | 99 |
| 9 | 20 | 32 | 46 | 63 | 89 | 96 | 99 |
| 10 | 22 | 43 | 55 | 67 | 93 | 97 | 99 |
| 11 | 27 | 40 | 54 | 65 | 89 | 96 | 98 |
| 12 | 17 | 29 | 44 | 56 | 85 | 94 | 99 |
| Mean | 17 | 30 | 43 | 57 | 86 | 98 | 101 |
| % RSD | 27.2 | 23.4 | 17.9 | 12.5 | 4.5 | 4.0 | 3.3 |

TABLE 22a

5% Ethyl Alcohol Medium Results - Acid Stage
(benzgalantamine (ALPHA-1062) delayed release tablets 15 mg)

| | % Dissolved | | | |
|---|---|---|---|---|
| Vessel | 30 Minutes | 60 Minutes | 90 Minutes | 120 Minutes |
| 1 | ND | ND | ND | ND |
| 2 | ND | ND | ND | ND |
| 3 | ND | ND | ND | ND |
| 4 | ND | ND | ND | ND |
| 5 | ND | ND | ND | ND |
| 6 | ND | ND | ND | ND |
| 7 | ND | ND | ND | ND |
| 8 | ND | ND | ND | ND |
| 9 | ND | ND | ND | ND |
| 10 | ND | ND | ND | ND |
| 11 | ND | ND | ND | ND |
| 12 | ND | ND | ND | ND |
| Mean | — | — | — | — |
| % RSD | — | — | — | — |

TABLE 22b

5% Ethyl Alcohol Medium Results - Buffer Stage
(benzgalantamine (ALPHA-1062) delayed release tablets 15 mg)

| | % Dissolved | | | | | | |
|---|---|---|---|---|---|---|---|
| Vessel | 15 Minutes | 20 Minutes | 25 Minutes | 30 Minutes | 45 Minutes | 60 Minutes | Infinity (+15 Minutes at 250 RPM) |
| 1 | 17 | 39 | 56 | 73 | 92 | 96 | 97 |
| 2 | 1 | 11 | 27 | 41 | 71 | 93 | 96 |
| 3 | 1 | 10 | 24 | 37 | 69 | 91 | 96 |
| 4 | 1 | 17 | 29 | 42 | 77 | 97 | 101 |
| 5 | 1 | 13 | 27 | 44 | 74 | 96 | 99 |
| 6 | 1 | 11 | 23 | 37 | 70 | 89 | 100 |
| 7 | 1 | 9 | 22 | 34 | 65 | 85 | 97 |
| 8 | 0 | 1 | 13 | 28 | 67 | 91 | 95 |
| 9 | 1 | 13 | 26 | 41 | 71 | 96 | 100 |
| 10 | 1 | 11 | 24 | 40 | 77 | 95 | 97 |
| 11 | 1 | 6 | 20 | 39 | 73 | 93 | 95 |
| 12 | 12 | 30 | 44 | 57 | 88 | 96 | 96 |
| Mean | 3 | 14 | 28 | 43 | 75 | 93 | 97 |
| % RSD | 170.8 | 73.1 | 40.8 | 27.4 | 10.9 | 3.9 | 2.1 |

TABLE 23a

20% Ethyl Alcohol Medium Results - Acid Stage
(benzgalantamine (ALPHA-1062) delayed release tablets 15 mg)

| | % Dissolved | | | |
|---|---|---|---|---|
| Vessel | 30 Minutes | 60 Minutes | 90 Minutes | 120 Minutes |
| 1 | ND | ND | ND | ND |
| 2 | ND | ND | ND | ND |
| 3 | ND | ND | ND | 1 |
| 4 | ND | ND | ND | ND |
| 5 | ND | ND | ND | ND |
| 6 | ND | ND | ND | ND |
| 7 | ND | ND | 1 | 3 |
| 8 | ND | ND | ND | ND |
| 9 | ND | 1 | 2 | 4 |
| 10 | ND | 1 | 1 | 5 |
| 11 | ND | ND | ND | ND |
| 12 | ND | ND | ND | ND |
| Mean | — | — | — | — |
| % RSD | — | — | — | — |

TABLE 23b

20% Ethyl Alcohol Medium Results - Buffer Stage
(benzgalantamine (ALPHA-1062) delayed release tablets 15 mg)

| | % Dissolved | | | | | | |
|---|---|---|---|---|---|---|---|
| Vessel | 15 Minutes | 20 Minutes | 25 Minutes | 30 Minutes | 45 Minutes | 60 Minutes | Infinity (+15 Minutes at 250 RPM) |
| 1 | 2 | 7 | 41 | 68 | 97 | 99 | 99 |
| 2 | 2 | 9 | 55 | 72 | 98 | 99 | 99 |
| 3 | 11 | 29 | 44 | 59 | 94 | 95 | 96 |
| 4 | 25 | 57 | 79 | 90 | 95 | 95 | 95 |
| 5 | 3 | 29 | 52 | 74 | 97 | 98 | 98 |
| 6 | 2 | 15 | 54 | 69 | 92 | 92 | 93 |
| 7 | 23 | 39 | 54 | 65 | 94 | 97 | 102 |
| 8 | 38 | 63 | 81 | 92 | 101 | 101 | 102 |
| 9 | 30 | 52 | 71 | 84 | 96 | 97 | 97 |
| 10 | 27 | 43 | 58 | 77 | 96 | 96 | 96 |
| 11 | 13 | 54 | 77 | 87 | 103 | 103 | 103 |
| 12 | 3 | 33 | 63 | 79 | 103 | 102 | 102 |
| Mean (12) | 15 | 36 | 61 | 76 | 97 | 98 | 99 |
| % RSD | 87.6 | 52.7 | 22.2 | 13.6 | 3.6 | 3.3 | 3.3 |

The inventive compositions (comprising 5 mg or 15 mg benzgalantamine) show no dissolution or dissolution of negligible amounts under acidic conditions (acid stage, pH 1.2) even in the presence of up to 20% (v/v) ethyl alcohol. Further, the compositions show no change in the release profile under buffered conditions (buffer stage, pH 6.8) in the presence of up to 20% (v/v) ethyl alcohol. These results demonstrate that the dissolution properties and the release of benzgalantamine from the inventive composition is not influenced by the presence of alcohol such as up to 20% (v/v) ethyl alcohol.

Example 5: Stability of Inventive Compositions

TABLE 24

Summary of stability results - Benzgalantamine (ALPHA-1062) delayed release tablets 5 mg.

| | | Storage (Test Interval Range) | | | | | |
|---|---|---|---|---|---|---|---|
| | | Batch 1 | | Batch 2 | | Batch 3 | |
| Attribute | Acceptance Criteria | 25° C./ 75% RH (range in 12 M) | 40° C./ 60% RH (range in 6 M) | 25° C./ 75% RH (range in 12 M) | 40° C./ 60% RH (range in 6 M) | 25° C./ 75% RH (range in 12 M) | 40° C./ 60% RH (range in 6 M) |
| Apperance | White to off-white, round, convex, coated tablet laser printed with B05 in grey packaged in a white, round, plastic bottle with pharmaceutical coil, desiccant, intact induction seal, and child resistant cap. | Conforms | Conforms | Conforms | Conforms | Conforms | Conforms |
| Assay | 90.0% to 110.0% of label claim (content uniformity) | 95.6 to 97.5 | 97.0 to 98.8 | 93.5 to 95.7 | 93.2 to 95.8 | 95.0 to 98.5 | 94.7 to 97.9 |
| Galantamine benzoylester N-oxide | no more than 0.5% | <0.10 to <0.10 | <0.10 to 0.19 | <0.10 to <0.10 | <0.10 to 0.15 | <0.10 to <0.10 | <0.10 to 0.18 |
| Any individual impurity | no more than 0.2% | <0.10 to <0.10 | <0.10 to <0.10 | <0.10 to <0.10 | <0.10 to <0.10 | <0.10 to <0.10 | <0.10 to <0.10 |
| Total impurities | No more than 1.5% | <0.10 to <0.10 | <0.10 to 0.20% | <0.10 to <0.10 | <0.10 to 0.2 | <0.10 to <0.10 | <0.10 to 0.2 |
| Dissolution | Acid stage, no individual release, >10% | 0 | 0 | 0 | 0 | 0 | 0 |
| | Buffer stage, not less than 80% (Q) release at 60 mir | 93 to 97 | 94 to 98 | 91 to 95 | 90 to 96 | 92 to 97 | 94 to 97 |
| Water content | For information only at time of test. Current acceptance criteria: not more than 2.0% | 0.37 to 1.37 | 0.57 to 0.89 | 0.32 to 1.20 | 0.38 to 0.55 | 0.35 to 1.37 | 0.42 to 0.49 |

RH: room humidity;
M: months.

TABLE 25

Summary of stability results - Benzgalantamine (ALPHA-1062) delayed release tablets 10 mg.

| | | Storage (Test Interval Range) | | | | | |
|---|---|---|---|---|---|---|---|
| | | Batch 1 | | Batch 2 | | Batch 3 | |
| Attribute | Acceptance Criteria | 25° C./ 75% RH (range in 12 M) | 40° C./ 60% RH (range in 6 M) | 25° C./ 75% RH (range in 12 M) | 40° C./ 60% RH (range in 6 M) | 25° C./ 75% RH (range in 12 M) | 40° C./ 60% RH (range in 6 M) |
| Apperance | Purple, round, convex, coated, laser printed B10 tablet, packaged in a white round plastic bottle with intact induction seal, desiccant and child resistant cap. Tablets may contain multi-colored specks. | Conforms | Conforms | Conforms | Conforms | Conforms | Conforms |
| Assay | 90.0% to 110.0% of label claim (content uniformity) | 97.6 to 100 | 97.5 to 98.4 | 98.8 to 99.6 | 97.5 to 103.2 | 94.7 to 101.8 | 94.7 to 97.5 |
| Galantamine benzoylester N-oxide | no more than 0.5% | <0.10 to 0.16 | <0.10 to 0.32 | <0.10 to <0.10 | <0.10 to 0.22 | <0.10 to <0.10 | <0.10 to 0.24 |
| Any individual impurity | no more than 0.2% | <0.10 to <0.10 | <0.10 to <0.10 | <0.10 to <0.10 | <0.10 to 0.14 | <0.10 to <0.10 | <0.10 to 0.15 |
| Total impurities | NMT 1.5% | <0.10 to 0.2 | <0.10 to 0.40 | <0.10 to <0.10 | <0.10 to 0.4 | <0.10 to <0.10 | <0.10 to 0.4 |
| Dissolution | Acid stage, no individual release, >10% | 0 | 0 | 0 | 0 | 0 | 0 |
| | Buffer stage, not less than 80% (Q) release at 60 min | 96 to 99 | 97 to 98 | 94 to 98 | 90 to 96 | 92 to 96 | 87 to 92 |
| Water content | For information only at time of test. Current acceptance criteria: no more than 2.0% | 0.61 to 1.20 | 0.57 to 1.05 | 0.45 to 1.56 | 0.45 to 0.55 | 0.46 to 1.52 | 0.49 to 0.54 |

RH: room humidity;
M: months

TABLE 26

Summary of stability results - Benzgalantamine (ALPHA-1062) delayed release tablets 15 mg.

| | | Storage (Test Interval Range) | | | | | |
|---|---|---|---|---|---|---|---|
| | | Batch 1 | | Batch 2 | | Batch 3 | |
| Attribute | Acceptance Criteria | 25° C./ 75% RH (range in 12 M) | 40° C./ 60% RH (range in 6 M) | 25° C./ 75% RH (range in 12 M) | 40° C./ 60% RH (range in 6 M) | 25° C./ 75% RH (range in 12 M) | 40° C./ 60% RH (range in 6 M) |
| Apperance | Gray, round, convex, coated, laser printed B15 tablet packaged in a white round plastic bottle with intact induction seal, desiccant and child resistantcap. Tablets may contain multi-colored specks | Conforms | Conforms | Conforms | Conforms | Conforms | Conforms |
| Assay | 90.0% to 110.0% of label claim (content uniformity) | 99.6 to 101.3 | 97.9 to 100.0 | 96.9 to 100.2 | 97.8 to 98.6 | 98.0 to 99.0 | 94.1 to 97.6 |
| Galantamineno benzoylesterthan N-oxide | more 0.5% | <0.10 to <0.10 | 0.11 to 0.23 | <0.10 to <0.10 | <0.10 to 0.24 | 0.49 to 0.54 | <0.10 to 0.24 |
| Any individual impurity | no more than 0.2% | <0.10 to <0.10 | <0.10 to <0.10 | <0.10 to <0.10 | <0.10 to <0.10 | <0.10 | <0.10 to 0.10 |
| Total impurities | no more than 1.5% | <0.10 to <0.10 | 0.11 to 0.2 | <0.10 to <0.10 | <0.10 to 0.2 | <0.10 | <0.10 to 0.2 |
| Dissolution | Acid stage, no individual release, >10% | 0 | 0 | 0 | 0 | 0 | 0 |
| | Buffer stage, not less than 80% (Q) release at 60 min | 97 to 102 | 91 to 94 | 88 to 96 | 81 to 88 | 91 to 94 | 83 to 95 |
| Water content | For information only at time of test. Current acceptance criteria: no more than 2.0% | 0.40 to 1.21 | 0.43 to 0.86 | 0.47 to 1.27 | 0.42 to 0.51 | 0.44 to 1.36 | 0.46 to 0.62 |

RH: relative humidity;
M: months

The inventive compositions comprising benzgalantamine (ALPHA-1062) gluconate as crystalline solid form A (anhydrous form) (5 mg, 10 mg and 15 mg) were tested for stability at 25° C./75% RH for 12 months and under accelerated conditions at 40° C./60% RH for 6 months.

The compositions showed high stability of the tablet formulation and API upon storage under the tested conditions. No impurities or decomposition products were detected, showing high chemical stability of benzgalantamine within the composition. Further, no changes in dissolution under acid stage and buffered stage were observed, when compared to the dissolution data shown in example 1 (measured after preparation of the compositions). Since API solubility (dissolution) is different for different crystalline forms of benzgalantamine gluconate, similar dissolution profiles at an initial time point (after preparation) and also after storage indicates no change in the crystalline form.

The compositions comprising benzgalantamine as crystalline solid form A (anhydrous form) thus possess high chemical and crystalline stability and advantageous dissolution properties even upon long term storage and under accelerated conditions.

REFERENCES

Baakman et al., First in human study with a prodrug of galantamine: Improved benefit-risk ratio?Alzheimers Dement (N Y). 2016 Jan. 20; 2(1):13-22.

Ho M D, Ring N, Amaral K, Doshi U, Li A R. Human Enterocytes as an In Vitro Model for the Evaluation of Intestinal Drug Metabolism: Characterization of Drug-Metabolizing Enzyme Activities of Cryopreserved Human Enterocytes from Twenty-Four Donors. Drug Metab Dispos. 2017 June; 45(6):686-691. doi: 10.1124/dmd.116.074377. Epub 2017 Apr. 10. PMID: 28396528.

Rudakova E V, Boltneva N P, Makhaeva G F. Comparative analysis of esterase activities of human, mouse, and rat blood. Bull Exp Biol Med. 2011 November; 152(1):73-5. English, Russian. doi: 10.1007/s10517-011-1457-y. PMID: 22803044.

Bakker C, van der Aart J, Hart E P, Klaassen E S, Bergmann K R, van Esdonk M J, Kay D G, Groeneveld G J. Safety, pharmacokinetics, and pharmacodynamics of Gln-1062, a prodrug of galantamine. Alzheimers Dement (N Y). 2020 Oct. 13; 6(1):e12093. doi: 10.1002/trc2.12093. PMID: 33083515; PMCID: PMC7551138.

What is claimed is:

1. A pharmaceutical composition in the form of a tablet, said tablet comprising:
   a. a tablet core, wherein said core comprises benzgalantamine or salt thereof, and
   b. an enteric coating comprises a copolymer of methacrylic acid and ethyl acrylate, wherein said enteric coating is configured for dissolution at pH 5.5 and above,
   wherein the tablet core is coated by a film coating in direct contact with the tablet core and is coated by the enteric coating, and
   wherein the composition shows at most 10% dissolution of benzgalantamine under acidic stage at pH 1.2 at 120 minutes, and at least 80% release of benzgalantamine under a buffered stage at pH 5.5 or 6.8 after 60 minutes in the dissolution test according to USP 711.

2. The pharmaceutical composition according to claim 1, wherein the tablet core further comprises a water-soluble filler.

3. The pharmaceutical composition according to claim 2, wherein the water-soluble filler is mannitol.

4. The pharmaceutical composition according to claim 1, wherein the tablet core further comprises a glidant.

5. The pharmaceutical composition according to claim 4, wherein the glidant is colloidal silicon dioxide.

6. The pharmaceutical composition according to claim 1, wherein the tablet core further comprises one or more lubricants.

7. The pharmaceutical composition according to claim 6, wherein the lubricant is sodium stearyl fumarate and/or magnesium stearate.

8. The pharmaceutical composition according to claim 1, wherein the film coating comprises hydroxypropyl methylcellulose (HPMC).

9. The pharmaceutical composition according to claim 8, wherein the film coating comprises HPMC and polyethylene glycol.

10. The pharmaceutical composition according to claim 1, wherein the benzgalantamine is a gluconate salt of benzgalantamine.

11. The pharmaceutical composition according to claim 10, wherein the benzgalantamine gluconate salt is present as crystalline solid form A (anhydrous form), wherein said crystalline form has prominent peaks at 3.61, 10.98, 14.41 and 18.44 degrees 2-theta (±0.2) in a powder X-ray diffraction pattern.

12. The pharmaceutical composition according to claim 1, wherein the tablet core comprises:
   benzgalantamine or salt thereof in an amount (wt % of the tablet core) of 5-20%,
   A water-soluble filler in an amount of 60-90%,
   A glidant in an amount of 0.1-5%, and
   One or more lubricants in an amount of 0.1-5%.

13. The pharmaceutical composition according to claim 12, wherein the tablet core comprises:
   benzgalantamine or salt thereof in an amount (wt % of the tablet core) of 10-15%,
   Mannitol in an amount of 70-90%,
   Colloidal silicon dioxide in an amount of 0.5-2%,
   Sodium stearyl fumarate in an amount of 14%, and
   Magnesium stearate in an amount of 0.5-2%.

14. The pharmaceutical composition according to claim 1, wherein the enteric coating is present in an amount, determined by weight gain in % in addition to the tablet core, of 5-20%.

15. The pharmaceutical composition according to claim 8, wherein the film coating is present in an amount, determined by weight gain in % in addition to the tablet core, of 2-10%.

16. The pharmaceutical composition according to claim 1, wherein
   a. the tablet core comprises:
      benzgalantamine or salt thereof in an amount (wt % of the tablet core) of 10-15%,
      Mannitol in an amount of 70-90%,
      Colloidal silicon dioxide in an amount of 0.5-2%,
      Sodium stearyl fumarate in an amount of 1-4%, and
      Magnesium stearate in an amount of 0.5-2%, and
   b. the enteric coating is present in an amount, determined by weight gain in % in addition to the tablet core, of 7-15%, and
   c. a film coating is present in an amount, determined by weight gain in % in addition to the tablet core, of 3-7%, and wherein said film coating is in direct contact with the tablet core and is coated by the enteric coating.

17. The pharmaceutical composition according to claim 1, wherein the composition is configured to release benzgalantamine after administration to a subject in the small intestine of said subject at pH 5.5 and above.

18. The pharmaceutical composition according to claim 1, wherein the composition shows at most 10% dissolution of benzgalantamine in the dissolution test according to USP 711 under acidic stage (pH 1.2) and in the presence of 20% (v/v) or less ethyl alcohol after 90 minutes.

19. The pharmaceutical composition according to claim 1, wherein after administration of the composition to a subject, benzgalantamine is at negligible levels or below a lower limit of detection in the plasma of the subject (exhibits complete or nearly complete conversion of benzgalantamine to Galantamine).

20. The composition according to claim 1, wherein after administration of the composition to a subject,
   a. a lower maximal plasma concentration ($c_{max}$) of Galantamine is obtained compared to an immediate release galantamine reference composition, and
   b. an area under the plasma curve (AUC) of Galantamine is obtained at 80-125% of the AUC for the reference composition,
   c. wherein said immediate release galantamine reference composition is a tablet comprising no coating or a coating configured for dissolution below pH 5.5 and a molar amount of Galantamine above the molar amount of galantamine in benzgalantamine in the pharmaceutical composition.

21. The composition according to claim 1, wherein after repeated administration of the composition to a subject,
   a. a greater maximal plasma concentration of Galantamine at steady state ($c_{max,ss}$) is obtained compared to an extended release galantamine reference composition, and
   b. an area under the plasma curve (AUC) of Galantamine is obtained at 80-125% of the AUC for the reference composition,
   c. wherein said extended release galantamine reference composition is a solid dosage form configured for extended release of Galantamine and comprising a molar amount of Galantamine above the molar amount of galantamine in benzgalantamine in the pharmaceutical composition.

22. The composition according to claim 1, wherein after administration of the composition to a subject, the subject has a likelihood of having a gastrointestinal adverse event equal to or less than 2%.

23. A method for the treatment of a brain disease associated with cognitive impairment and/or with a cholinergic deficit, comprising administering the pharmaceutical composition according to claim 1 to a subject in need thereof.

24. The method according to claim 23, wherein the brain disease is selected from the group consisting of a brain disease with a cholinergic deficit, a brain disease with a cholinergic deficit, Alzheimer's disease, Parkinson's disease, dementia, schizophrenia, epilepsy, stroke, poliomyelitis, neuritis, myopathy, oxygen and nutrient deficiencies in the brain after hypoxia, anoxia, asphyxia, cardiac arrest, chronic fatigue syndrome, poisoning, anesthesia, spinal cord disorders, central inflammatory disorders, Lewy Body Disease, multiple sclerosis, skeletal muscle pain, autism, Rett's syndrome, motor neuron disease such as amyotrophic lateral sclerosis, traumatic brain injury, post-traumatic stress disorder, postoperative delirium, neuropathic pain, abuse of alcohol and drugs, addictive alcohol and/or nicotine craving, severe gas in the gastro-intestinal tract (GIT), constipation, low blood pressure, erratic heart rate, and effects of radiotherapy.

25. A method for preparing a pharmaceutical composition in the form of a tablet according to claim 1, wherein said composition is prepared by blending components of the tablet core to form a blend, compressing said blend to form a tablet core, coating said tablet core with a film coating, and coating said film coating with an enteric coating.

* * * * *

UNITED STATES PATENT AND TRADEMARK OFFICE
CERTIFICATE OF CORRECTION

| | | |
|---|---|---|
| PATENT NO. | : 12,208,167 B1 | |
| APPLICATION NO. | : 18/434155 | |
| DATED | : January 28, 2025 | |
| INVENTOR(S) | : Michael McFadden et al. | |

It is certified that error appears in the above-identified patent and that said Letters Patent is hereby corrected as shown below:

In the Specification

In Column 5, Lines 54-55, delete
"at values above 7.
In one embodiment," and insert --at values above 7. In one embodiment,--.

In Column 6, Lines 39-40, delete
"U.S. Ser. No. 11/795,176B2),
which" and insert --U.S. Patent No. 11,795,176 B2), which--.

In Column 7, Lines 8-9 (Approx.), delete
"X-ray diffraction pattern.
These peaks" and insert --X-ray diffraction pattern. These peaks--.

In Column 7, Lines 32-33 (Approx.), delete
"inventive
compositions.
Further" and insert --inventive compositions. Further,--.

In Column 7, Line 39, delete "A water-soluble" and insert --a water-soluble--.

In Column 7, Line 40 (Approx.), delete "A glidant" and insert --a glidant--.

In Column 7, Line 41 (Approx.), delete "One or" and insert --one or--.

In Column 13, Line 39 (Approx.), delete "of –90% and" and insert --of ~90% and--.

In Column 13, Line 61 (Approx.), delete "benzazepin-6 benzoate gluconate" and insert --benzazepin-6-benzoate gluconate--.

Signed and Sealed this
First Day of April, 2025

Coke Morgan Stewart
*Acting Director of the United States Patent and Trademark Office*

CERTIFICATE OF CORRECTION (continued)

In Column 13, Line 67 (Approx.), delete "of prodrug" and insert --of prodrug.--.

In Column 20, Line 47, delete "0.12 aW, for" and insert --0.12 $a_w$, for--.

In Column 24, Line 8, delete "(HPC, hyprollose), hydroxypropyl" and insert --(HPC, hypromellose), hydroxypropyl--.

In Column 24, Line 10, delete "(HPC, hyprollose), sodium" and insert --(HPC, hypromellose), sodium--.

In Column 32, Line 30 (Approx.), delete "(Benzgalantamine (APLPHA-1062)" and insert --(Benzgalantamine (ALPHA-1062)--.

In Column 32, Line 38 (Approx.), delete "Release (OR) 5" and insert --Release (DR) 5--.

In Column 36, Line 8 (Approx.), delete "using Phoenix®® WinNonlin®" and insert --using Phoenix® WinNonlin®--.

In Column 36, Line 26 (Approx.), delete "$k_{el}$, $AUC_{0-t}$ $AUC_{0-\infty}$, AUC" and insert "$k_{el}$, $AUC_{0-t}/AUC_{0-\infty}$, AUC--.

In Column 36, Line 27 (Approx.), delete "$t_{1/2}$, $T_{lagg}$, Vz/F" and insert --$t_{1/2}$, $T_{lag}$, Vz/F--.

In Columns 35-36, Line 40 (Approx.), delete "state con- centration is" and insert --state concentration is--.

In Column 39, Line 48, delete "90% Cl of" and insert --90% CI of--.

In Column 39, Line 55, delete "90% Cl for" and insert --90% CI for--.

In Column 40, Line 49, delete "(90% Cl within" and insert --(90% CI within--.

In Column 42, Line 35 (Approx.), delete "$K_{el}$, $T_{1/2}$" and insert --$K_{el}$, $T_{1/2}$.--.

In Column 44, Line 47 (Approx.), delete "on Day1 was" and insert --on Day 1 was--.

In Column 47, Line 32 (Approx.), delete "hours), $C_{trough}$(concentration at" and insert --hours), $C_{trough}$ (concentration at--.

In Column 47, Line 48 (Approx.), delete "90% Cl for" and insert --90% CI for--.

In Column 49, Line 29 (Approx.), delete "90% Cl of" and insert --90% CI of--.

In Column 49, Line 34 (Approx.), delete "90% Cl for" and insert --90% CI for--.

CERTIFICATE OF CORRECTION (continued)
U.S. Pat. No. 12,208,167 B1

In Column 49, Line 56 (Approx.) (TABLE 17), delete "1 (2.5 %)" and insert --1 (2.5%)--.

In Column 50, Line 21 (Approx.), delete "(90% Cl within" and insert --(90% CI within--.

In Column 51, Line 42 (Approx.) (TABLE 18b), under header "Vessel", delete "1" and insert --4--.

In Columns 53-54, Line 55 (Approx.) (TABLE 20b), under header "60 Minutes", delete "771" and insert --77[1]--.

In Column 55, Line 3 (Approx.) (TABLE 21a), delete "(benzgalantamine (ALPJHA-1062)" and insert --benzgalantamine (ALPHA-1062)--.

In Columns 59-60, Line 22 (Approx.) (TABLE 24), delete "Apperance" and insert --Appearance--.

In Columns 61-62, Line 12 (Approx.) (TABLE 25), delete "Apperance" and insert --Appearance--.

In Columns 63-64, Line 12 (Approx.) (TABLE 26), delete "Apperance" and insert --Appearance--.

In Columns 63-64, Line 25 (Approx.) (TABLE 26), delete "resistantcap." and insert --resistant cap.--.

In Columns 63-64, Line 36 (Approx.) (TABLE 26), delete "Galantamineno" and insert --Galantamine--.

In Columns 63-64, Line 36 (Approx.) (TABLE 26), delete "more" and insert --no more than--.

In Columns 63-64, Line 37 (Approx.) (TABLE 26), delete "benzoylesterthan" and insert --benzoylester--.

In Columns 63-64, Line 37 (Approx.) (TABLE 26), delete "0.5%" and insert --than 0.5%--.

In Column 65, Line 6, delete "Li A R. Human" and insert --Li A P. Human--.

In Column 65, Line 20, delete "of Gin-1062," and insert --of Gln-1062,--.

In the Claims

In Column 66, Claim 12, Line 8, delete "A water-soluble" and insert --a water-soluble--.

In Column 66, Claim 12, Line 9, delete "A glidant" and insert --a glidant--.

In Column 66, Claim 12, Line 10, delete "One or more" and insert --one or more--.

In Column 66, Claim 13, Line 17, delete "of 14%, and" and insert --of 1-4%, and--.